(12) United States Patent
Handy et al.

(10) Patent No.: US 6,997,863 B2
(45) Date of Patent: *Feb. 14, 2006

(54) THERMOTHERAPY VIA TARGETED DELIVERY OF NANOSCALE MAGNETIC PARTICLES

(75) Inventors: Erik S. Handy, Arlington, MA (US); Robert Ivkov, Marblehead, MA (US); Diane Ellis-Busby, Lancaster, MA (US); Allan Foreman, Epping, NH (US); Susan J. Braunhut, Wellesley, MA (US); Douglas U. Gwost, Shoreview, MN (US); Blair Ardman, Marblehead, MA (US)

(73) Assignee: Triton BioSystems, Inc., Chelmsford, MA (US)

( * ) Notice: Subject to any disclaimer, the term of this patent is extended or adjusted under 35 U.S.C. 154(b) by 577 days.

This patent is subject to a terminal disclaimer.

(21) Appl. No.: 10/200,082

(22) Filed: Jul. 19, 2002

(65) Prior Publication Data
US 2003/0032995 A1    Feb. 13, 2003

Related U.S. Application Data

(63) Continuation-in-part of application No. 10/176,950, filed on Jun. 18, 2002.

(60) Provisional application No. 60/307,785, filed on Jul. 25, 2001.

(51) Int. Cl.
*A61N 2/00* (2006.01)

(52) U.S. Cl. .................................... 600/9; 977/DIG. 1

(58) Field of Classification Search ............. 600/9–15; 607/103, 105; 424/422–423, 426, 428, 430, 424/434–437, 489–491, 493–502, 647–648, 424/1.29, 1.33, 1.53, 9.32–9.323; 977/DIG. 1
See application file for complete search history.

(56) References Cited

U.S. PATENT DOCUMENTS 4,106,488 A    8/1978    Gordon (Continued)

FOREIGN PATENT DOCUMENTS

EP    0040512 A    11/1981

(Continued)

OTHER PUBLICATIONS

Peasley, K.W. "Destruction of human immunodeficiency-infected cells by ferrofluid particles manipulated by an external magnetic field: mechanical disruption and selective introduction of cytotoxic or antiretroviral substances into target cells." Medical Hypotheses, 1996, pp. 5-12, vol. 46, No. 1, England (ABSTRACT).

(Continued)

*Primary Examiner*—John P. Lacyk
(74) *Attorney, Agent, or Firm*—Raymond A. Miller; Pepper Hamilton LLP; Lucy Elandjian

(57) ABSTRACT

Disclosed are therapeutic methods for the treatment of disease material involving administration of a thermotherapeutic magnetic composition, which contains single-domain magnetic particles attached to a target-specific ligand, to a patient and application of an alternating magnetic field to inductively heat the thermotherapeutic magnetic composition. Also disclosed are methods of administering the thermotherapeutic magnetic material composition. The thermotherapeutic methods may be used where the predetermined target is associated with diseases, such as cancer, diseases of the immune system, and pathogen-borne diseases, and undesirable targets, such as toxins, reactions associated with organ transplants, hormone-related diseases, and non-cancerous diseased cells or tissue.

79 Claims, 8 Drawing Sheets

U.S. PATENT DOCUMENTS

| | | |
|---|---|---|
| 4,303,636 A | 12/1981 | Gordon |
| 4,312,364 A | 1/1982 | Convert |
| 4,323,056 A | 4/1982 | Borrelli |
| 4,392,040 A | 7/1983 | Rand |
| 4,452,773 A | 6/1984 | Molday |
| 4,454,234 A | 6/1984 | Czerlinski |
| 4,545,368 A | 10/1985 | Rand |
| RE32,066 E | 1/1986 | Leveen |
| 4,569,836 A | 2/1986 | Gordon |
| 4,574,782 A | 3/1986 | Borrelli |
| 4,590,922 A | 5/1986 | Gordon |
| 4,610,241 A | 9/1986 | Gordon |
| 4,622,952 A | 11/1986 | Gordon |
| 4,662,359 A | 5/1987 | Gordon |
| 4,678,667 A | 7/1987 | Meares |
| 4,708,718 A | 11/1987 | Daniels |
| 4,735,796 A | 4/1988 | Gordon |
| 4,753,894 A | 6/1988 | Frankel |
| 4,758,429 A | 7/1988 | Gordon |
| 4,767,611 A | 8/1988 | Gordon |
| 4,813,399 A | 3/1989 | Gordon |
| 4,889,120 A | 12/1989 | Gordon |
| 4,923,437 A | 5/1990 | Gordon |
| 4,950,221 A | 8/1990 | Gordon |
| 4,983,159 A | 1/1991 | Rand |
| 4,996,991 A | 3/1991 | Gordon |
| 5,043,101 A | 8/1991 | Gordon |
| 5,067,952 A | 11/1991 | Gudov et al. |
| 5,087,438 A | 2/1992 | Gordon |
| 5,099,756 A | 3/1992 | Franconi |
| 5,128,147 A | 7/1992 | Leveen |
| 5,169,774 A | 12/1992 | Frankel |
| 5,203,782 A | 4/1993 | Gudov |
| 5,300,750 A | 4/1994 | Carter, Jr. et al. |
| 5,411,730 A | 5/1995 | Kirpotin |
| 5,441,746 A | 8/1995 | Chagnon |
| 5,468,210 A | 11/1995 | Matsui |
| 5,506,343 A | 4/1996 | Kufe |
| 5,547,682 A | 8/1996 | Chagnon |
| 5,612,019 A | 3/1997 | Gordon |
| 5,620,480 A | 4/1997 | Rudie |
| 5,622,686 A | 4/1997 | Gordon |
| 5,629,197 A | 5/1997 | Ring |
| 5,658,234 A | 8/1997 | Dunlavy |
| 5,677,171 A | 10/1997 | Hudziak |
| 5,705,157 A | 1/1998 | Greene |
| 5,720,954 A | 2/1998 | Hudziak |
| 5,772,997 A | 6/1998 | Hudziak |
| 5,859,206 A | 1/1999 | Vandlen |
| 5,891,996 A | 4/1999 | Mateo de Acosta del Rio |
| 5,916,539 A | 6/1999 | Pilgrimm |
| 5,922,845 A | 7/1999 | Deo |
| 5,935,866 A | 8/1999 | Chagnon |
| 5,958,374 A | 9/1999 | Meares |
| 5,968,511 A | 10/1999 | Akita |
| 6,008,203 A | 12/1999 | Magnani |
| 6,015,567 A | 1/2000 | Hudziak |
| 6,037,129 A | 3/2000 | Cole |
| 6,054,561 A | 4/2000 | Ring |
| 6,074,337 A | 6/2000 | Tucker |
| 6,149,576 A | 11/2000 | Gray |
| 6,165,440 A | 12/2000 | Esenaliev |
| 6,165,464 A | 12/2000 | Hudziak |
| 6,167,313 A | 12/2000 | Gray |
| 6,190,870 B1 | 2/2001 | Schmitz |
| 6,242,196 B1 | 6/2001 | Spiegelman |
| 6,252,050 B1 | 6/2001 | Ashkenazi |
| 6,281,202 B1 | 8/2001 | Magnani |
| 6,303,755 B1 | 10/2001 | Deo |
| 6,344,203 B1 | 2/2002 | Sandrin |
| 6,347,633 B1 | 2/2002 | Groth |
| 6,387,371 B1 | 5/2002 | Hudziak |
| 6,387,888 B1 | 5/2002 | Mincheff |
| 6,391,026 B1 | 5/2002 | Hung |
| 6,541,039 B1 * | 4/2003 | Lesniak et al. ............. 424/647 |
| 6,638,494 B1 * | 10/2003 | Pilgrimm ................. 424/9.323 |
| 2002/0052594 A1 | 5/2002 | Goldenberg |

FOREIGN PATENT DOCUMENTS

| | | |
|---|---|---|
| EP | 0136530 | 4/1985 |
| EP | 0333381 | 9/1989 |
| EP | 0400940 | 12/1990 |
| EP | 0543498 | 5/1993 |
| EP | 00344270 B1 | 11/1994 |
| EP | 0913167 A2 | 5/1999 |
| EP | 0673255 B1 | 8/2001 |
| JP | 1244767 | 9/1989 |
| WO | WO9411023 | 5/1994 |
| WO | WO 97/43005 | 11/1997 |
| WO | WO 99/19000 | 4/1999 |
| WO | WO 00/52714 | 9/2000 |
| WO | WO 01/500 A1 | 2/2001 |
| WO | WO 01/501 A1 | 2/2001 |
| WO | WO 01/17611 | 3/2001 |
| WO | WO 01/37721 | 5/2001 |

OTHER PUBLICATIONS

Torchilin, V.P., et al. "Magnetic sephadex as a carrier for enzyme immobilization and drug targeting." Journal of Biomedical Materials Research, 1985, pp. 461-466, vol. 19, No. 4, United States (ABSTRACT).

Molina, M.A., et al. "Trastuzumab (herceptin), a humanized anti-Her2 receptor monoclonal antibody, inhibits basal and activated Her2 ectodomain cleavage in breast cancer cells." Cancer Research 2001, pp. 4744-4749, Jun. 15;61(12) (ABSTRACT).

Wong, C., et al. "Human scFv antibody fragments specific for the epithelial tumour marker MUC-1, selected by phage display on living cells." Cancer Immunol. Immunother. 2001, pp. 93-101, Apr.;50(2). (ABSTRACT).

Winthrop, M.D., et al. "Development of a hyperimmune anti-MUC-1 single chain antibody fragment phage display library for targeting breast cancer." Clinical Cancer Research 1999, pp. 3088-3094, Oct.;5(10 suppl.).

Richman, C.M., et al. "Systemic radiotherapy in metastatic breast cancer using 90Y-linked monoclonal MUC-1 antibodies." Crit Rev Oncol Hematol 2001,pp. 25-35, vol. 38, Ireland (ABSTRACT).

Kobayashi, T., et al. "Targeting hyperthermia for renal cell carcinoma using human MN antigen-specific magnetoliposomes". Japanese Journal of Cancer Research 2001 vol. 92 No. 10 (ABSTRACT).

Young, A.J., et al. "A pulsed power supply system for producing high intensity magnetic and electric fields for medical applications". IEEE Conference Record—Abstracts. PPPS-2001 Pulsed Power Plasma Science 2001. 28th IEEE International Conference on Plasma Science and 13th IEEE International Pulsed Power Conference (Cat. No. 01CH37255) 2001, pp. 322 USA (ABSTRACT).

Peterson, J.A., et al. "Effect of multiple, repeated doses of radioimmunotherapy on target antigen expression (breast MUC-1 mucin) in breast carcinomas", Cancer Res. 1997, pp. 1103-1108, vol. 57(6), (ABSTRACT).

Diaz, A.K., et al. "Expression of epithelial mucins Muc1, Muc2, and Muc3 in ductal carcinoma in situ of the breast", Breast J. 2001, pp. 40-45, vol. 7(1), (ABSTRACT).

Barratt-Boyles, S.M. "Making the most of mucin: a novel target for tumor immunotherapy", Cancer Immunol. Immunother. 1996, pp. 142-151, vol. 43(3), (ABSTRACT).

Menard, S.M., et al. "Role of Her2 gene overexpression in breast carcinoma", J. Cell Physiol. 2000, pp. 150-162, vol. 182(2), (ABSTRACT).

Hadden, J.W., "The immunology and immunotherapy of breast cancer: an update", Int. J. Immunopharacol. 1999, pp. 79-101, vol. 21(2), (ABSTRACT).

Tucker, R.D., et al. "Defining the heating characteristics of ferromagnetic implants using calorimetry" J. of Biomedical Materials Research, 2000, vol. 53, pp. 791-798. (ABSTRACT).

Takegami, K., et al. "New ferromagnetic bone cement for local hyperthermia" J. Biomedical Materials Research, 1998, vol. 43, pp. 210-214. .(ABSTRACT).

Paulus, J.A., et al. "Corrosion analysis of NiCu and PdCo thermal seed alloys used as interstitial hyperthermia implants", 1997, vol. 18, pp. 1609-1614. .(ABSTRACT).

Graef, G.L. "Materials for low Curie temperature induction heating of tumors (Hyperthermia)" Ph.D. Dissertation, University of Arizona, 1991 .(ABSTRACT).

Petrarca, C. et al. "Isolation of MUC1-primed B lymphocytes from tumour-draining lymph nodes by immunomagnetic beads". Cancer Immunology Immunotherapy 1999 pp. 272-277 vol. 47 No. 5 (ABSTRACT).

Shinkai, M., et al. "Targeting hyperthermia for renal cell carcinoma using human mn antigen-specific magnetoliposomes" Jpn. J. Cancer Res., 2001, vol. 92, pp. 1138-1145. (ABSTRACT).

Suzuki, M., et al. "Preparation and characteristics of magnetite-labelled antibody with the use of poly(ethylene glycol), derivatives". Biotechnol Appl Biochem., 1995, vol. 21, pp. 335-345.

Shinkai, M., et al. "Antibody-conjugated magnetoliposomes for targeting cancer cells and their application in hyperthermia". Biotechnol Appl Biochem 1994 vol. 21, pp. 125-137.

Jordan, A., et al. "Magnetic fluid hyperthermia (MFH): Cancer treatment with AC magnetic field induced excitation of biocompatible superparamagnetic nanoparticles". J. Magnetism and Magnetic Materials 1999, pp. 413-419, vol. 201.

Jordan, A., et al. "Inductive heating of ferromagnetic particles and magnetic fluids: physical evaluation of their potential for hyperthermia". Int. J. Hyperthermia 1993, pp. 51-68, vol. 9.

Jordan, A., et al. "Magnetic Fluid Hyperthermia (MFH)", in *Scientific and Clinical Applications of Magnetic Carriers*, Hafeli et al., eds. 1997, pp. 569-595, USA.

Chan, D.C.F., et al. "Synthesis and evaluation of colloidal magnetic iron oxides for the site-specific radiofrequency-induced hyperthermia of cancer". J. Magnetism and Magnetic Materials, 1993, pp. 374-378, vol. 122, Holland.

Brusentsov, N.A., et al. "Evaluation of ferromagnetic fluids and suspensions for the site-specific radiofrequency-induced hyperthermia of MX11 sarcoma cells in vitro" J. Magnetism and Magnetic Materials, 2001, vol. 225, pp. 113-117.

Jones, S.K., et al. "Experimental examination of a targeted hyperthermia system using inductively heated ferromagnetic microspheres in rabbit kidney" Physics in Medicine and Biology, 2001, vol. 46, pp. 385-398.

Jones, S.K., et al. "Evaluation of ferromagnetic materials for low-frequency hysteresis heating of tumors" Physics in Medicine and Biology, 1992, vol. 37, pp. 293-299.

Moroz, P., et al. "Targeting liver tumors with hyperthermia: Ferromagnetic embolization in a rabbit liver tumor model" J. of Surgical Oncology, 2001, vol. 78, pp. 22-29.

Hiergeist, R., et al. "Application of magnetic ferrofluids for hyperthermia" J. Magnetism and Magnetic Materials, 1999, vol. 201, pp. 420-422.

Shinkai, M., et al."Intracellular hyperthermia for cancer using magnetite cationic liposomes: In vitro study" Jpn. J. Cancer Research, 1996, vol. 87, pp. 1179-1183.

Carter, P., "Improving the efficacy of antibody-based cancer therapies", Nature Reviews 2001, pp. 118-129, vol. 1.

McDevitt, M., et al. "Tumor therapy with targeted atomic nanogenerators", Science 2001, pp. 1537-1550, vol. 294.

Segal, D.M., et al. "Introduction: bispecific antibodies", J. Immunol. Methods 2001, pp. 1-6, vol. 248.

Reiter, Y., et al. "Recombinant immunotoxins in targeted cancer cell therapy", Adv. Cancer Res. 2001, pp. 93-124.

Hergt, R.W.T., et al."Physical limits of hyperthermia using magnetite fine particles" IEEE Trans. On Mag., 1998, vol. 34, pp. 3745-3754.

Hynynen, K., et al. "State of the art in medicine: Hyperthermia in cancer treatment" Investigative Radiology, 1990, vol. 2, 824-834.

Jordan, A., et al. "Cellular uptake of magnetic fluid particles and their effects on human adenocarcinoma cells exposed to AC magnetic fields in vitro" Int. J. Hyperthermia, 1996, vol. 12, pp. 705-722.

Chan, D.C.F., et al. "Physical chemistry and in vivo tissue heating properties of colloidal magnetic iron oxides with increased power adsorption rates" in *Scientific and Clinical Applications of Magnetic Carriers*, Hafeli et al., eds. 1997, pp. 607-618, Plenum Press, New York, USA.

Suzuki, S. et al. "Studies on liposomal ferromagnetic particles and a technique of high frequency inductive heating" Jpn. J. Soc. Cancer Ther., 1990, vol. 25, pp. 2649-2658.

Gordon, R.T., et al. "Intracellular hyperthermia: a biophysical approach to cancer treatment via intracellular temperature and biophysical alterations" Medical Hypothesis, 1979, vol. 5, pp. 83-102.

Goldin, J.H., et al. "The effects of diapulse on the healing of wounds: a double-blind randomized controlled trial in man" Brit. J. of Plastic Surgery, 1981, vol. 34, pp. 267-270.

Gilchrist, R.K., et al. "Selective inductive heating of lymph nodes" Annals of Surgery, 1957, vol. 146, pp. 596-606.

Luderer, A.A., et al. "Glass-ceramic-mediated, magnetic-field-induced localized hyperthermia: Response of a murine mammary carcinoma" Radiation Research, 1983, vol. 94, pp. 190-198.

Bartlett, K., et al. "On the use of ferromagnetic microparticles in microwave and radio frequency hyperthermia" J. of the Inst. of Electronic and Radio Engineers, 1988, vol. 58, pp. 197-201.

Bacri, J.C., et al. "Use of magnetic nanoparticles for thermolysis of cells in a ferrofluid" in *Scientific and Clinical Applications of Magnetic Carriers*, Hafeli et al., eds. 1997, pp. 597-606, Plenum Press, New York, USA.

Mitsumori, M., et al. "Targeted hyperthermia using dextran magnetite complex: A new treatment modality for liver tumors" Hepato-Gastroenterology, 1996, vol. 43, pp. 1431-1437.

Borrelli, N.F., et al. "Hysteresis heating for the treatment of tumours". Phys Med Biol. 1984, pp. 487-494, vol. 29, No. 5, England.

Mitsumori, M., et al. "Development of intra-arterial hyperthermia using a dextran-magnetite complex" Int. J. Hyperthermia, 1994, vol. 10, pp. 785-793.

Csuka,O., et al. "Prognostic factors of breast cancer" Magy. Onkol., 2000, vol. 44, pp. 53-60. ABSTRACT.

Luftner, D., et al. "Nuclear matrix proteins as biomarkers for breast cancer" Expert Rev. Mol. Diagn., 2002, vol. 2, pp. 23-31. ABSTRACT.

Krishnamurthy, S., et al. "Molecular and biologic markers of premalignant lesions of human breast" Adv. Anat. Pathol., 2002, vol. 9, pp185-197. ABSTRACT.

Palmu, S., et al. "Expression of C-KIT and HER-2 tyrosine kinase receptors in poor-prognosis breast cancer" Anticancer Res., 2002, vol. 22, pp 411-414. ABSTRACT.

Esteva, F.J., et al. "Expression of erbB/HER receptors, heregulin and P38 in primary breast cancer using quantitative immunohistochemistry" Pathol. Oncol. Res., 2002, vol. 7, pp. 171-177. ABSTRACT.

O'Hanlon, D.M., et al. "An immunohistochemical study of p21 and p53 expression in primary node-positive breast carcinoma" Eur. J. Surg. Oncol., 2002, vol. 28, pp. 103-107. ABSTRACT.

Aguilar, Z., et al. "The transmembrane heregulin precursor is functionally active" J. Biol. Chem., 2001, vol. 276, pp. 44099-44107. ABSTRACT.

DeFazio, A., et al. "Expression of c-erbB receptors, heregulin and estrogen receptor in human breast cell lines" Int. J. Cancer, 2000, vol. 87, pp. 487-498. ABSTRACT.

Hadden, J.W., "The immunology and immunotherapy of breast cancer: an update" Int. J. Immunopharmacol., 1999, vol. 21, pp. 79-101. ABSTRACT.

Gion, M., et al. "CA27.29: a valuable marker for breast cancer management. A confirmatory multicentric study on 603 cases" Eur. J. Cancer, 2001, vol. 37, pp. 355-363. ABSTRACT.

Suo, Z., et al. "EGFR family expression in breast carcinomas. C-erbB-2 and c-erbB-4 receptors have different effects on survival" J. Pathol., 2002, vol. 196, pp. 17-25. ABSTRACT.

Parker, C., et al. "E-cadherin as a prognostic indicator in primary breast cancer" Br. J. Cancer, vol. 85, pp. 1958-1963. ABSTRACT.

Lakhani, S.R., et al. "The pathology of familial breast cancer: predictive value of immunohistochemical markers estrogen receptor, progesterone receptor, HER-2, and p53 in patients with mutations in BRCA1 and BRCA2" J. Clin. Oncol., 2002, vol. 20, pp. 2310-2318. ABSTRACT.

Moritani, S., et al. "Availability of CD10 immunohistochemistry as a marker of breast myoepithelial cells on paraffin sections" Mod. Pathol., 2002, vol. 15, pp. 397-405. ABSTRACT.

Spizzo, G., et al. "Prognostic significance of Ep-CAM and Her-2/neu Overexpression in invasive breast cancer" Int. J. Cancer, 2002, vol. 98, pp. 883-888. ABSTRACT.

Van Poznak, C., et al. "Assessment of molecular markers of clinical sensitivity to single-agent taxane therapy for metastatic breast cancer" J. Clin. Oncol., vol. 20, pp. 2319-2326. ABSTRACT.

Opezzo, P., et al. "Production and functional characterization of two mouse/human chimeric antibodies with specificity for the tumor associated Tn antigen" Hibridoma, 2000, vol. 19, pp. 229-239. ABSTRACT.

Babino, A., et al. "Tn antigen is a pre-cancerous biomarker in breast tissue and serum in n-nitrosomethylurea-induced rat carcinogenesis" Int. J. Cancer, 2000, vol. 86, pp. 753-759. ABSTRACT.

Lapetti, M., et al. "Controlling tumor-derived and vascular endothelial cell growth: role of the 4Ff2 cell surface antigen" Am. J. Pahol., 2001, vol. 159, pp. 165-178. ABSTRACT.

Molina, M.A., et al. "Tastuzumab (herceptin) a humanized anti-Her2 receptor monoclonal antibody, inhibits basal and activated Her2 ectodomain cleavage in breast cancer cells" Cancer Res., 2001, vol. 61, pp. 4744-4749. ABSTRACT.

Wong, C., et al. "Human scFv antibody fragments specific for the epithelial tumor marker MUC-1, selected by phage display on living cells" Cancer Immunol. Immunother., 2001, vol. 50, pp. 93-101. ABSTRACT.

Isaacs, J.D., et al. "Humanized monoclonal antibody therapy for rheumatoid arthritis" Lancet, 1992, vol. 240, pp. 748-752. ABSTRACT.

Isaacs, J.D., et al. "Humanized anti-CD4 monoclonal antibody therapy of autoimmune and inflammatory disease" Clin. Exp. Immunol., 1997, vol. 110, pp. 158-166. ABSTRACT.

Coles, A.J., et al. "Pulsed monoclonal antibody treatment and autoimmune thyroid disease in multibple sclerosis" Lancet, 1999, vol. 354, pp. 1691-1695. ABSTRACT.

Moseley, R.P., et al. "HMFG1 antigen: a new marker for carcinomatous meningitis" Int. J. Cancer, 1989, vol. 44, pp. 440-444. ABSTRACT.

Stockhammer, G., et al. "Vascular endothelial growth factor in CSF: a biological marker for carcinomatous meningitis" Neurology, 2000, vol. 54, pp. 1670-1676. ABSTRACT.

Gourevitch, M.M., et al. "Polymorphic epithelial mucin (MUC-1)-containing circulating immune complexes in carcinoma patients" Br. J. Cancer, 1995, vol. 72, pp. 934-938. ABSTRACT.

Ramakrishna, V., et al. "Generation and phenotypic characterization of new human ovarian cancer cell lines with the identification of antigens potentially recognizable by HLA-restricted cytotoxic T cells" Int. J. Cancer, 1997, vol. 73, pp. 143-150. ABSTRACT.

Snijdewint, F.G., et al. "Cellular and humoral immune responses to MUC1 mucin and tandem-repeat peptides in ovarian cancer patients and controls" Cancer Immunol. Immunother., 1999, vol. 48, pp. 47-55. ABSTRACT.

Wu, X., et al. "Activated matrix metalloproteinase-2—a potential marker of prognosis for epithelial ovarian cancer" Gynecol. Oncol., 2002, vol. 84, pp. 126-134. ABSTRACT.

Taylor, D.D., et al. "Shed membrane fragment-associated markers for endometrial and ovarian cancers" Gynecol. Onccol., 2002, vol. 84, pp. 443-448. ABSTRACT.

Davidson, B. "Ovarian carcinoma and serous effusions. Changing views regarding tumor progression and review of current literature" Anal. Cell Pathol., 2001, vol. 23, pp. 107-128. ABSTRACT.

Jiang, X.P., et al. "Vaccination with a mixed vaccine of autogenous and allogenic breast cancer cells and tumor associated antigens CA15-3, CEA and CA125—results in immune and clinical responses in breast cancer patients" Cancer Biother. Radiopharm., 2000, vol. 15, pp. 495-505. ABSTRACT.

Garcia-Pachon, E., et al. "Diagnositic value of C-reactive protein in exudative pleural effusions" Eur. J. Intern. Med., 2002, vol. 13, pp. 246-249. ABSTRACT.

Ma, Z., et al. "Molecular cloning and expression analysis of feline melanoma antigen (MAGE) obtained from a lymphoma cell line" Vet. Immunol. Immunopathol., 2001, vol. 83, pp. 241-252. ABSTRACT.

Barker, P.A., et al. "The MAGE proteins: emerging roles in cell cycle progression, apoptosis, and neurogenic disease" J. Neurosci. Res., 2002, vol. 67, pp. 705-712. ABSTRACT.

McTernan, P.G., et al. "Increased resistin gene and protein expression in human abdominal adipose tissue" J. Clin. Endocrinol. Metab., 2002, vol. 87, pp. 2407. ABSTRACT.

Xu, H., et al. "Altered tumor necrosis factor-alpha (TNF-alpha) processing in adipocytes and increased expression of transmembrane TNF-alpha in obesity" Diabetes, 2002, vol. 51, pp. 1876-1883. ABSTRACT.

George, J., et al. "Functional inhibition of Ras by S-trans, trans-farnesyl thiosalicylic acid attenuates atherosclerosis in apolipoprotein E knockout mice" Circulation, 2002, vol. 105, pp. 2416-2422. ABSTRACT.

Ibrahimi, A., et al. "Role of CD36 in membrane transport of long-chain fatty acids" Curr. Opin. Clin. Nutr. Metab. Care, 2002, vol. 5, pp. 139-145. ABSTRACT.

Miyawaki, K., et al. "Inhibition of gastric inhibitory polypeptide signaling prevents obesity" Nat. Med., 2002, vol. 8, pp. 738-742. ABSTRACT.

International Search Report for PCT/US02/23650.

Jordan et al., *Magnetic Fluid Hyperthermia (MFH), Scientific and Clinical Applications of Magnetic Carriers*, 1997, pp. 569-595.

* cited by examiner

THERMOTHERAPY VIA TARGETED DELIVERY OF NANOSCALE MAGNETIC PARTICLES

CROSS REFERENCE TO RELATED APPLICATION

This is a non-provisional application claiming the benefit of and priority to a provisional patent application with Ser. No. 60/307,785 filed on Jul. 25, 2001, and also claiming priority to a Continuation-in-Part application with Ser. No. 10/176,950 filed on Jun. 18, 2002, both of which are incorporated herein by reference.

TECHNICAL FIELD

The present invention relates generally to thermotherapy, more specifically, to magnetic material compositions, devices for use with magnetic material compositions, and methods related thereto for thermotherapy via targeted delivery of nanoscale magnetic particles.

BACKGROUND

The time between the onset of disease in a patient and the conclusion of a successful course of therapy is often unacceptably long. Many diseases remain asymptomatic and evade detection while progressing to advanced and often terminal stages. In addition, this period may be marked by significant psychological and physical trauma for the patient due to the unpleasant side effects of even correctly prescribed treatments. Even those diseases that are detected early may be most effectively treated only by therapies that disrupt the normal functions of healthy tissue or have other unwanted side effects.

One such disease is cancer. Despite considerable research effort and some success, cancer is still the second leading cause of death in the United States, claiming more than 500,000 lives each year according to American Cancer Society estimates. Traditional treatments are invasive and/or are attended by harmful side effects (e.g., toxicity to healthy cells), often making for a traumatic course of therapy with only modest success. Early detection, a result of better diagnostic practices and technology, has improved the prognosis for many patients. However, the suffering that many patients must endure makes for a more stressful course of therapy and may complicate patient compliance with prescribed therapies. Further, some cancers defy currently available treatment options, despite improvements in disease detection. Of the many forms of cancer that still pose a medical challenge, prostate, breast, lung, and liver claim the vast majority of lives each year. Colorectal cancer, ovarian cancer, gastric cancer, leukemia, lymphoma, melanoma, and their metastases may also be life-threatening.

Conventional treatments for breast cancer, for example, typically include surgery followed by radiation and/or chemotherapy. These techniques are not always effective, and even if effective, they suffer from certain deficiencies. Surgical procedures range from removal of only the tumor (lumpectomy) to complete removal of the breast. In early stage cancer, complete removal of the breast provides the best assurance against recurrence, but is disfiguring and requires the patient to make a very difficult choice. Lumpectomy is less disfiguring, but is associated with a greater risk of cancer recurrence. Radiation therapy and chemotherapy are arduous and are not completely effective against recurrence.

Treatment of pathogen-based diseases is also not without complications. Patients presenting symptoms of systemic infection are often mistakenly treated with broad-spectrum antibiotics as a first step. This course of action is completely ineffective when the invading organism is viral. Even if a bacterium (e.g., *E. coli*) is the culprit, the antibiotic therapy eliminates not only the offending bacteria, but also benign intestinal flora in the gut that are necessary for proper digestion of food. Hence, patients treated in this manner often experience gastrointestinal distress until the benign bacteria can repopulate. In other instances, antibiotic-resistant bacteria may not respond to antibiotic treatment. Therapies for viral diseases often target only the invading viruses themselves. However, the cells that the viruses have invaded and "hijacked" for use in making additional copies of the virus remain viable. Hence, progression of the disease is delayed, rather than halted.

For these reasons, it is desirable to provide improved and alternative techniques for treating disease. Such techniques should be less invasive and traumatic to the patient than the present techniques, and should only be effective locally at targeted sites, such as diseased tissue, pathogens, or other undesirable matter in the body. Preferably, the techniques should be capable of being performed in a single or very few treatment sessions (minimizing the need for patient compliance), with minimal toxicity to the patient. In addition, the undesirable matter should be targeted by the treatment without requiring significant operator skill and input.

Immunotherapy is a rapidly expanding type of therapy used for treating a variety of human diseases including cancer, for example. The FDA has approved a number of antibody-based cancer therapeutics. The ability to engineer antibodies, antibody fragments, and peptides with altered properties (e.g., antigen binding affinity, molecular architecture, specificity, valence, etc.) has enhanced their use in therapies. Cancer immunotherapeutics have made use of advances in the chimerization and humanization of mouse antibodies to reduce immunogenic responses in humans. High affinity human antibodies have also been obtained from transgenic mice that contain many human immunoglobulin genes. In addition, phage display technology, ribosome display, and DNA shuffling have allowed for the discovery of antibody fragments and peptides with high affinity and low immunogenicity for use as targeting ligands. All of these advances have made it possible to design an immunotherapy that has a desired antigen binding affinity and specificity, and minimal immune response.

The field of cancer immunotherapy makes use of markers that are over-expressed by cancer cells (relative to normal cells) or expressed only by cancer cells. The identification of such markers is ongoing and the choice of a ligand/marker combination is critical to the success of any immunotherapy. Immunotherapeutics fall into three classes: (1) deployment of antibodies that, themselves, target growth receptors, disrupt cytokine pathways, or induce complement or antibody-dependent cytotoxicity; (2) direct arming of antibodies with a toxin, a radionuclide, or a cytokine; (3) indirect arming of antibodies by attaching them to immunoliposomes used to deliver a toxin or by attaching them to an immunological cell effector (bispecific antibodies). Although armed antibodies have shown potent tumor activity in clinical trials, they have also exhibited unacceptably high levels of toxicity to patients.

The disadvantage of therapies that rely on delivery of immunotoxins or radionuclides (i.e., direct and indirect arming) has been that, once administered to the patient, these agents are active at all times. (A "therapy-on-demand"

approach would be preferable.) These therapies often cause damage to non-tumor cells and present toxicity issues and delivery challenges. For example, cancer cells commonly shed surface-expressed antigens (targeted by immunotherapeutics) into the blood stream. Immune complexes can be formed between the immunotherapeutic and the shed antigen. As a result, many antibody-based therapies are diluted by interaction with these shed antigens instead of interacting with the cancer cells themselves, reducing the true delivered dose.

Temperatures in a range from about 40° C. to about 46° C. (hyperthermia) can cause irreversible damage to disease cells. However, healthy cells are capable of surviving exposure to temperatures up to around 46.5° C. Diseased tissue may be treated by elevating the temperature of its individual cells to a lethal level (cellular thermotherapy). Pathogens implicated in disease and other undesirable matter in the body can be also be destroyed via exposure to locally-high temperatures.

Hyperthermia may hold promise as a treatment for cancer because it induces instantaneous necrosis (typically called "thermo-ablation") and/or a heat-shock response in cells (classical hyperthermia), leading to cell death via a series of biochemical changes within the cell. State-of-the-art systems that employ radio-frequency (RF) hyperthermia, such as annular phased array systems (APAS), attempt to tune E-field energy for regional heating of deep-seated tumors. Such techniques are limited by the heterogeneities of tissue electrical conductivity and that of highly perfused tissue. This leads to the as-yet-unsolved problems of "hot spot" phenomena in untargeted tissue with concomitant underdosage in the desired areas. These factors make selective heating of specific regions with such E-field dominant systems very difficult.

Another strategy that utilizes RF hyperthermia requires surgical implantation of microwave or RF based antennae or self-regulating thermal seeds. In addition to its invasiveness, this approach provides few (if any) options for treatment of metastases because it requires knowledge of the precise location of the primary tumor. The seed implantation strategy is thus incapable of targeting undetected individual cancer cells or cell clusters not immediately adjacent to the primary tumor site. Clinical success of this strategy is hampered by problems with the targeted generation of heat at the desired tumor tissues.

SUMMARY OF THE INVENTION

Hyperthermia for treatment of disease using magnetic fluids exposed to RF fields has been recognized for several decades. However, a major problem with magnetic fluid hyperthermia has been the inability to selectively deliver a lethal dose of particles to the cells or pathogens of interest.

In view of the above, there is a need for a hyperthermia-based method for treating diseased tissue, pathogens, or other undesirable matter, that incorporates selective delivery of thermotherapeutic magnetic compositions and magnetic fields to a target within a patient's body. It is also desirable to have treatment methods that are safe and effective, short in duration, and require minimal invasion.

It is, therefore, an object of the present invention to provide a treatment method that involves the administration of a magnetic material composition, which contains single-domain magnetic particles attached to a target-specific ligand, to a patient and the application of an alternating magnetic field to inductively heat the magnetic material composition.

It is another object of the present invention to provide such a treatment method that includes the detection of at least one location of accumulation of the magnetic material composition within the patient's body prior to the application of an alternating magnetic field.

It is another object of the present invention to provide such a treatment method that involves the application of the alternating magnetic field when the magnetic material composition is outside the patient's body.

It is another object of the present invention to provide a treatment method that involves the induction of a desired pathological effect by inductively heating the magnetic material to cause a necrosis, an apoptosis, or deactivation of disease material.

It is yet another object of the present invention to provide a method for administration of the magnetic material composition, which may be intraperitoneal injection, intravascular injection, intramuscular injection, subcutaneous injection, topical, inhalation, ingestion, rectal insertion, wash, lavage, rinse, or extracorporeal administration into patient's bodily materials.

It is a further object of the present invention to provide methods for the treatment of tissue in a safe and effective manner, with minimal invasion, and short treatment periods.

The present invention pertains to methods for treating disease material in a patient. In one embodiment, a treatment method is disclosed that involves the administration of a thermotherapeutic magnetic composition, which contains single-domain magnetic particles attached to a target-specific ligand, to a patient and the application of an alternating magnetic field to inductively heat the magnetic material composition. The thermotherapeutic magnetic composition may also be administered by administering the ligand and the magnetic particle separately to the patient, and then combining the ligand and the magnetic particle in the patient's body.

In another embodiment, a treatment method is disclosed that involves the administration of the thermotherapeutic magnetic composition, detecting at least one location of accumulation of the thermotherapeutic magnetic composition within the patient's body, and the application of an alternating magnetic field to inductively heat the thermotherapeutic magnetic composition.

In another embodiment, a treatment method is disclosed that involves the administration of the thermotherapeutic magnetic composition to a patient, and application of an alternating magnetic field to induce a desired pathological effect by inductively heating the thermotherapeutic magnetic to cause a necrosis, an apoptosis, or a pathogen deactivation.

In another embodiment, a treatment method is disclosed that involves the administration of the thermotherapeutic magnetic composition, which may be intraperitoneal injection, intravascular injection, intramuscular injection, subcutaneous injection, topical, inhalation, ingestion, rectal insertion, wash, lavage or rinse perisurgically, or extracorporeal administration into patient's bodily materials.

Any of the disclosed embodiments may include treatment methods including monitoring of at least one physical characteristic of a portion of a patient.

Any of the disclosed embodiments may include treatment methods where the predetermined target is associated with diseases, such as cancer, diseases of the immune system, and pathogen-borne diseases, and undesirable targets, such as toxins, reactions to organ transplants, hormone-related diseases, and non-cancerous diseased cells or tissue.

The above summary of the present invention is not intended to describe each illustrated embodiment or every implementation of the present invention. The figures and the detailed description which follow particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 9b schematically illustrates the design of a coil for use in the embodiment illustrated in FIG. 9a.

Figure 1:
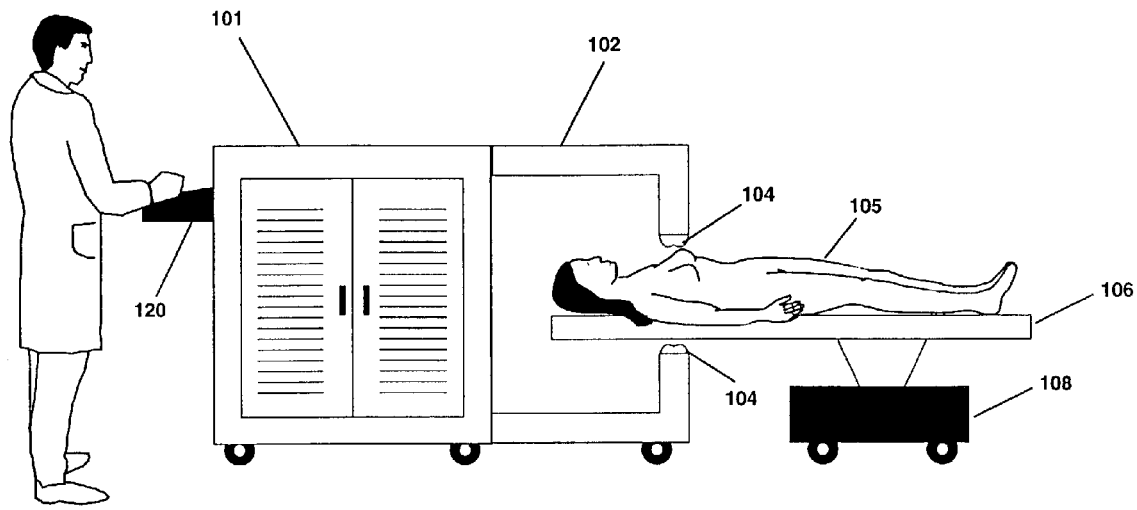
FIG. 1 schematically illustrates a thermotherapy treatment system according to an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention pertains to magnetic material compositions, devices for treating diseased, disease-causing, or undesirable tissue or material, for use with magnetic material compositions, and methods for treating or removing the tissue or material utilizing such devices and magnetic material compositions. Diseased, disease-causing, or undesirable material in the body are referred to herein as "disease material". The therapeutic methods disclosed herein include the targeted delivery of nanometer sized magnetic particles to the target material. The term "bioprobe", as used herein, refers to the composition including a magnetic particle, a biocompatible coating material, and a target-specific ligand. The term "ligand", as used herein, refers to compounds which target biological markers. Examples of ligands include proteins, peptides, antibodies, antibody fragments, saccharides, carbohydrates, glycans, cytokines, chemokines, nucleotides, lectins, lipids, receptors, steroids, neurotransmitters, Cluster Designation/Differentiation (CD) markers, imprinted polymers, and the like. The methods for treating disease material disclosed herein include administering to a patient the bioprobes suspended in an appropriate medium, and applying, via a device capable of interacting with the bioprobes, an alternating magnetic field to an area of the patient containing the bioprobes to heat the bioprobes sufficiently to kill or render ineffective the disease material.

One embodiment of the invention, as illustrated in FIG. 1, includes an alternating magnetic field (AMF) generator located within a cabinet 101 designed to produce an alternating magnetic field (AMF) that may be guided to a specific location within a patient 105 by a magnetic circuit 102. The therapeutic methods of the present invention may be performed following a determination of the presence of disease material in one or more areas of the patient. For example, the disease material may be any one or combination of cancers and cancerous tissue, a pathogenic infection (viral, bacterial or multicellular parasitic), toxin, or any pathogen-like material (prion). The manner of making the diagnosis does not form part of the invention and may be performed using any standard method. However, the present invention, or aspects thereof, may be amenable to a diagnostic function alone or in conjunction with another method or apparatus. Such a diagnostic function would be performed by using a suitable technology or technique to interrogate the magnetic properties of the bioprobes, and thus evaluate their concentration and location within the patient. Both the location and concentration of bioprobes may be determined using an existing technique such as magnetic resonance imaging, or another diagnostic technique can be established and performed using a suitable magnetometer, such as a Superconducting Quantum Interference Device (SQUID). Information obtained from this interrogation may be used to define the parameters of treatment, i.e. the location, duration, and intensity, of the alternating magnetic field. The patient lies upon an X-Y horizontal and vertical axis positioning bed 106. The bed 106 is both horizontally and vertically positionable via a bed controller 108. The AMF generator produces an AMF in the magnetic circuit 102 that exits the magnetic circuit at one pole face 104, passing through the air gap and the desired treatment area of the patient, and reenters the circuit through the opposing pole face 104, thus completing the circuit. An operator or medical technician is able to both control and monitor the AMF characteristics and bed positioning via the control panel 120.

Figure 2:
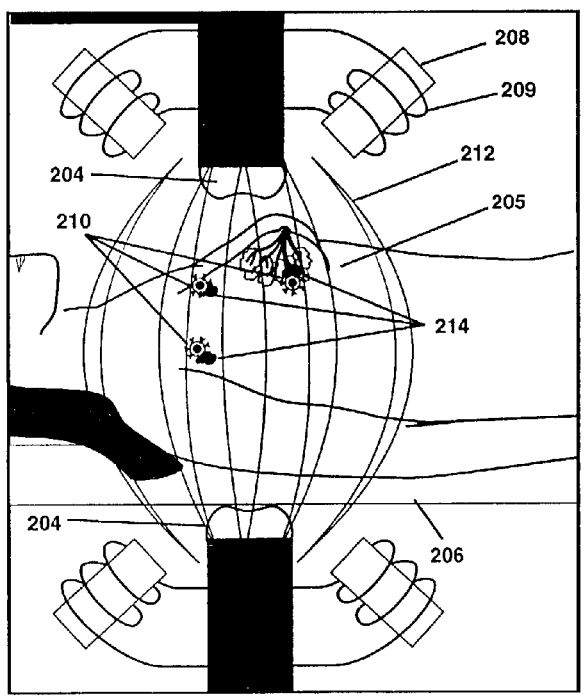
FIG. 2 schematically illustrates a thermotherapy treatment according to an embodiment of the present invention.

FIG. 2 illustrates a treatment of a patient with a device for treating disease material according to an embodiment of the present invention. The area of the patient to be treated 205 is localized in the region between the magnetic poles 204 via the positionable bed 206. This region may be any location of the patient including the chest, abdomen, head, neck, back, legs, arms, any location of the skin. An AMF may be applied to the treatment area 205 of the patient, as illustrated by the magnetic lines of flux 212. The magnetic field, manifested by the magnetic lines of flux 212 interacts with both healthy and disease material in the localized area. Bioprobes 210, containing at least one appropriate ligand selective to the particular type of disease material, are bound to the disease material 214. In the illustrated case, the bioprobes 210 are selective to breast cancer. The bioprobes 210 become excited by the interacting applied AMF and are inductively heated to a temperature sufficient to kill or render ineffective the disease material. For example, heat generated in the bioprobes 210 may pass to the cells, thereby causing the cells to die.

Furthermore, the poles 204 may be formed from pieces whose gap is adjustable, so as to permit other parts of the body to be treated. It is advantageous to set the gap between the poles 204 to be sufficiently large to permit the part of the body containing the disease material to enter the gap, but not be so large as to reduce the magnetic field strength. Also shown are secondary coils 208 and optional cores 209. Any number of these may be added to modify the distribution of magnetic flux produced by the primary coils and the core. The secondary coils 208 may be wired in series or in parallel with the primary coils, or they can be driven by separate AMF generators. The phase, pulse width and amplitude of the AMF generated by these coils may be adjusted to maximize the field strength in the gap, minimize the field strength in areas which may be sensitive to AMF, or to uniformly distribute the magnetic field strength in a desired manner.

Figure 3:
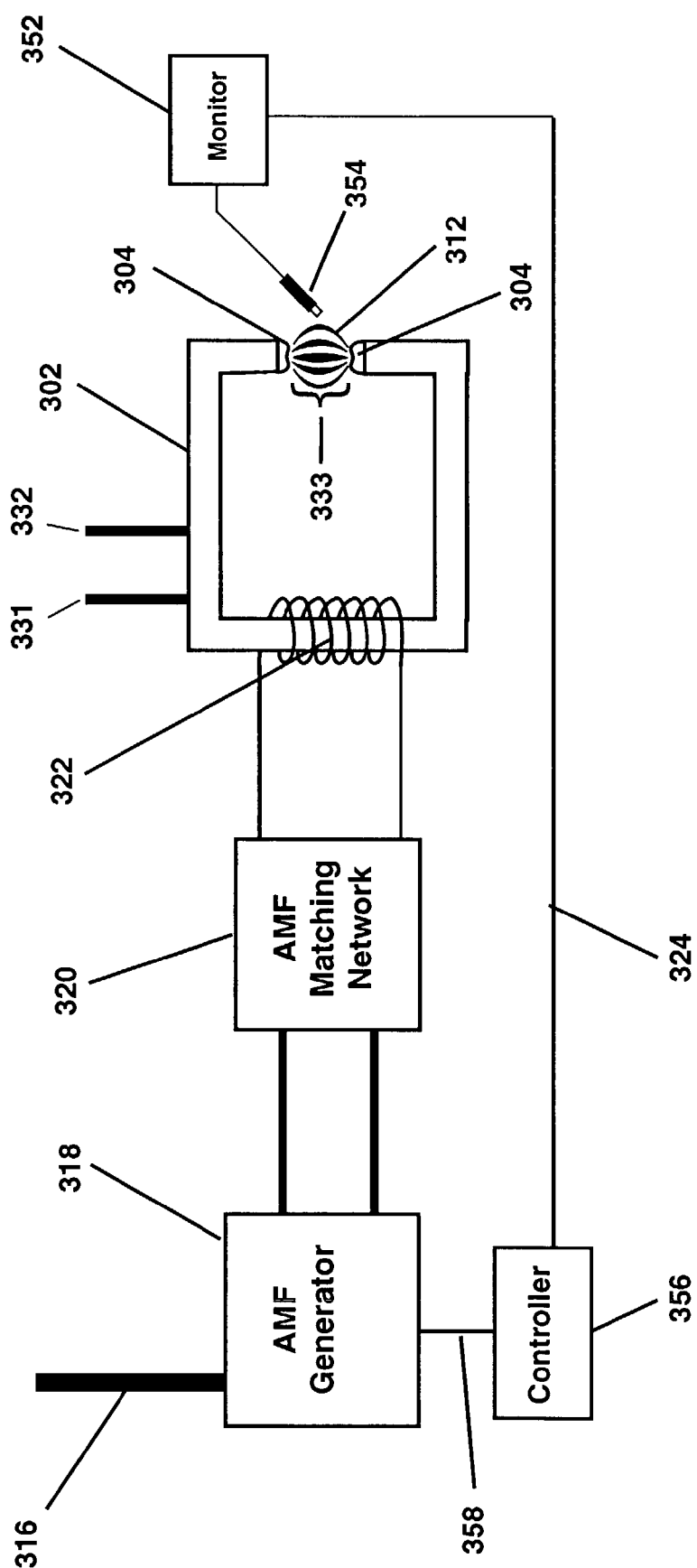
FIG. 3 schematically illustrates a circuit for producing a thermotherapeutic alternating magnetic field according to an embodiment of the present invention.

FIG. 3 illustrates a circuit for producing an AMF according to an embodiment of the present invention. The AMF generator 318 is supplied with alternating current (AC) power via the conduit 316. A circulating fluid supply is also provided in the conduit 316. The AMF generator 318 may become hot, and it may be cooled with the circulating fluid supply while in operation. The fluid may be water; however a fluid such as silicone oil or other inorganic or organic fluids with suitable thermal and electric properties may be preferable to increase generator efficiency. The energy produced by the generator 318 is directed through the AMF matching network 320 where the impedance of the generator is matched to the impedance of the coil 322. The impedance of the AMF matching network 320 may be adjustable to minimize the energy reflected back to the generator 318. In another embodiment, the generator frequency may be automatically adjusted to minimize the reflected energy. The modified energy may be directed to the magnetic circuit 302. An AMF is induced in the magnetic circuit 302 as a result of the current passing through the solenoid coil 322. Magnetic lines of flux 312 are produced in the gap 333 between the poles 304 in the magnetic circuit 302. Items 331 and 332 illustrate a liquid cooling send and return.

A feedback loop 324 may be provided for monitoring the magnetic field profile in the gap 333 between the poles 304. The probe 354 may provides data to the monitor 352, which relays information to the controller 356 via an appropriate data bus 324. Information from the controller 356 is relayed to the generator 318 via an appropriate data bus 358. Monitoring the magnetic field profile may be useful in detecting the presence of magnetic particles, monitoring an inductance of tissue, and monitoring the temperature of tissue located in the gap 333.

Figure 4A:
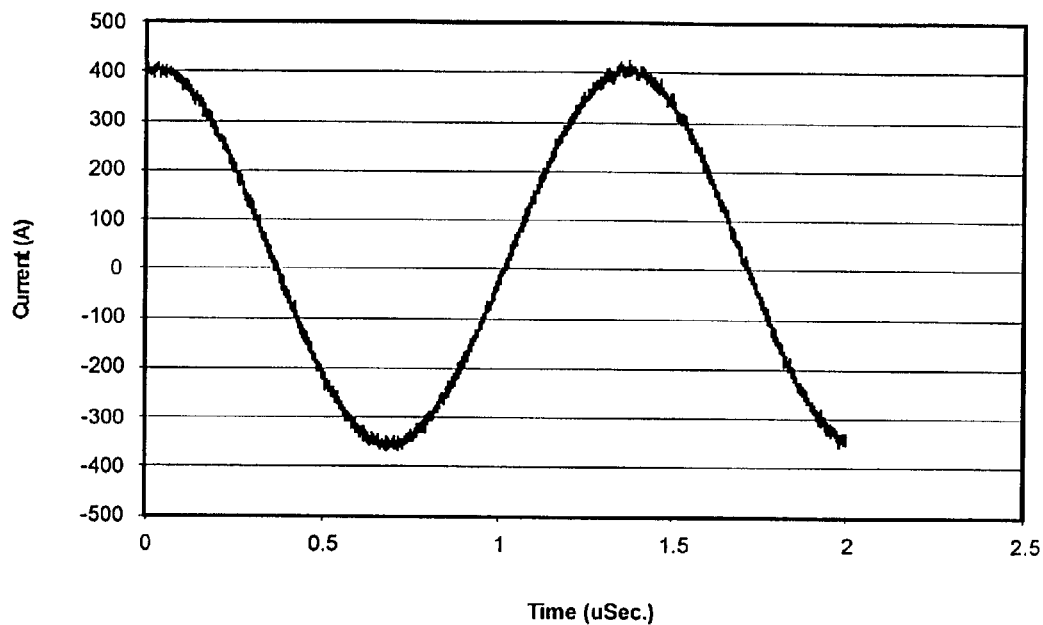
FIG. 4a graphically illustrates a thermotherapeutic sinusoidal current waveform according to an embodiment of the present invention.
Figure 4B:
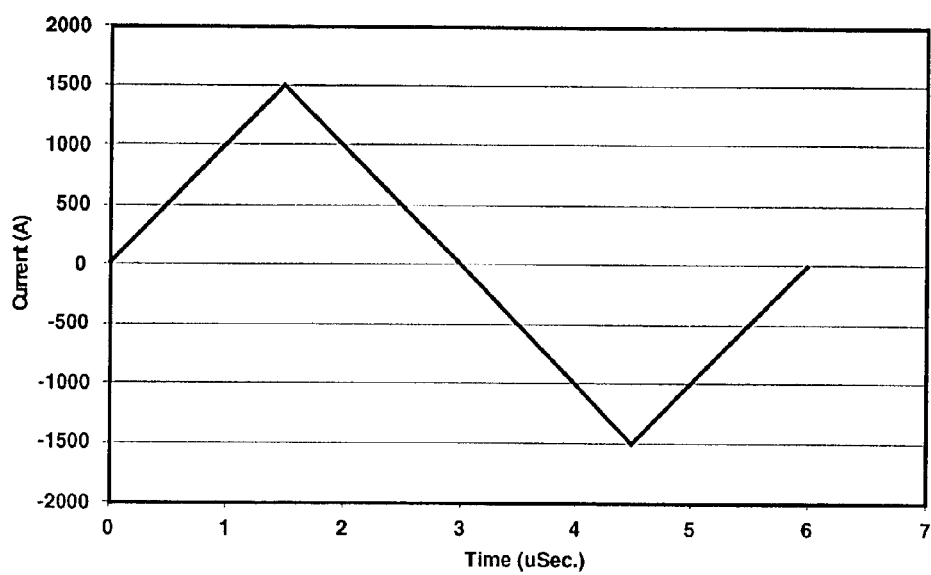
FIG. 4b graphically illustrates a thermotherapeutic triangular current waveform according to an embodiment of the present invention.

Measuring alternating magnetic fields directly is extremely difficult. Because the AMF is proportional to the current in the coil 322, characteristics of the AMF may be defined in terms of the coil current, which can readily be measured with available test equipment. For example, the coil current may be viewed and measured with a calibrated Rogowski coil and any oscilloscope of suitable bandwidth. The fundamental waveform may be observed as the direct measure of the magnitude and direction of the coil current. Many different types of fundamental waveforms may be used for the AMF. For example, FIG. 4a illustrates a sinusoidal current waveform, and FIG. 4b illustrates a triangular current waveform. The shape of the fundamental waveform may also be square, sawtooth, or trapezoidal.

Most practical generators produce an approximation of these waveforms with some amount of distortion. In most applications, this waveform may be nearly symmetrical around zero, as illustrated in FIGS. 4a and 4b. However, there may be a static (DC) current, known as a DC offset, superimposed on the waveform. An AMF with a DC offset can be used to influence the movement of bioprobes within the body. With a suitable gradient and the "vibration-like" effect of the AC component, the bioprobes are typically drawn toward the area of highest field strength. FIGS. 4a and 4b show at least one cycle of two different fundamental waveforms with zero or near zero DC offsets. The fundamental period may be defined as the time it takes to complete one cycle. The fundamental frequency may be defined as the reciprocal of the fundamental period. The fundamental frequency may be between 1 kHz and 1 GHz, preferably between 50 kHz and 15 MHz, and more preferably between 100 kHz and 500 kHz. The fundamental frequency may be intentionally modulated, and may often vary slightly as a result of imperfections in the RF generator design.

Figure 5A:
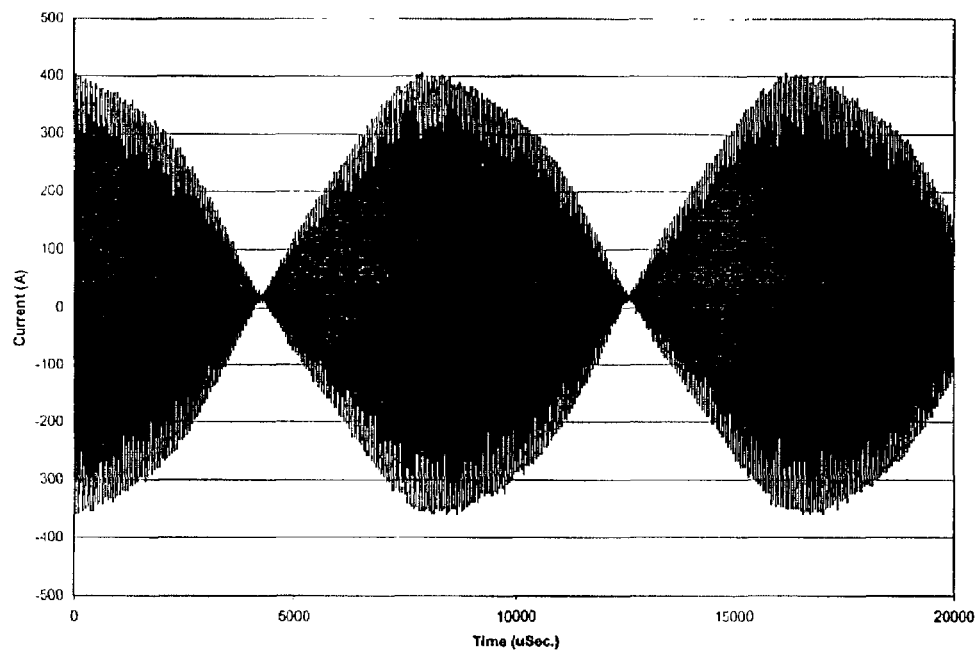
FIG. 5a graphically illustrates a thermotherapeutic sinusoidal waveform modulation according to an embodiment of the present invention.
Figure 5B:
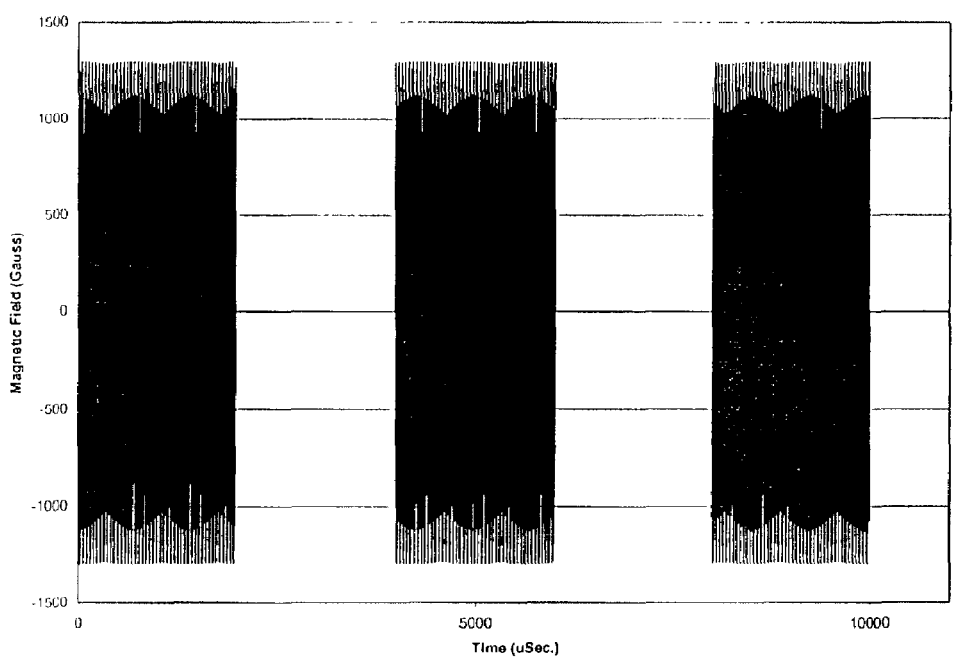
FIG. 5b graphically illustrates a thermotherapeutic pulsed waveform modulation according to an embodiment of the present invention.

The amplitude of the waveform may also be modulated. FIG. 5a illustrates an embodiment in which a sinusoidal current modulation envelope may be used, and FIG. 5b illustrates an embodiment that utilizes a square modulation envelope. The shape of the amplitude modulation envelope may typically be sinusoidal, square, triangular, trapezoidal or sawtooth, and may be any variation or combination thereof, or may be some other shape.

The AMF produced by the generator may also be pulsed. Pulse width is traditionally defined as the time between the −3 dBc points of the output of a square law crystal detector. Because this measurement technique is cumbersome in this application, we use an alternate definition of pulse width. For the purpose of this invention, pulse width may be defined as the time interval between the 50% amplitude point of the pulse envelope leading edge and the 50% amplitude point of the pulse envelope trailing edge. The pulse width may also be modulated.

The pulse repetition frequency (PRF) is defined as the number of times per second that the amplitude modulation envelope is repeated. The PRF typically lies between 0.0017 Hz and 1000 MHz. The PRF may also be modulated. The duty cycle may be defined as the product of the pulse width and the PRF, and thus is dimensionless. In order to be defined as pulsed, the duty of the generator 318 must be less than unity (or 100%).

The AMF may be constrained to prevent heating healthy tissue to lethal temperatures, for example by setting the temperature of the tissue to be around 43° C., thus allowing for a margin of error of about 3° C. from the temperature of 46.5° C. that is lethal to healthy tissue. This may be accomplished in a variety of ways.

The peak amplitude of the AMF may be adjusted.
The PRF may be adjusted.
The pulse width may be adjusted.
The fundamental frequency may be adjusted.
The treatment duration may be adjusted.

These four characteristics may be adjusted to maximize the heating rate of the bioprobes and, simultaneously, to minimize the heating rate of the healthy tissue located within the treatment volume. These conditions may vary depending upon tissue types to be treated, thus the operator may determine efficacious operation levels. In one embodiment, one or more of these characteristics may be adjusted during treatment based upon one or more continuously monitored physical characteristics of tissue in the treatment volume by the probe 354, such as temperature or impedance. This information may then be supplied as input to the generator 318, via the monitor 352, the data bus 324, the controller 356, and the data bus 358 to control output, constituting the feedback loop. In another embodiment, one or more physical characteristics of the bioprobes (such as magnetic properties) may be monitored during treatment with a suitable device. In this case, one or more magnetic property, such as the magnetic moment, is directly related to the temperature of the magnetic material. Thus, by monitoring some combination of magnetic properties of the bioprobe, the bioprobe temperature can be monitored indirectly. This information may also be supplied as input to the generator 318, via the monitor 352, the data bus 324, the controller 356, and the data bus 358 to control output to become part of the feedback loop. The generator output may be adjusted so that the peak AMF strength is between about 10 and about 10,000 Oersteds (Oe). Preferably, the peak AMF strength is between about 20 and about 3000 Oe, and more preferably, between about 100 and about 2000 Oe.

In another embodiment of the present invention, the differential heating of the bioprobes, as compared to that of the healthy tissue, may be maximized. The bioprobes 210 heat in response to each cycle of the AMF. Assuming the fundamental frequency, the PRF, and the pulse width remain constant, the heat output of the bioprobe 210 continues to increase as peak amplitude of the AMF increases until the magnetic material of the bioprobe reaches saturation. Beyond this point, additional increases in AMF amplitude yield almost no additional heating. At AMF amplitudes below saturation however, it can be said that bioprobe heating is a function of AMF amplitude. Unlike bioprobes, healthy tissue heating is a result of eddy current flow and a function of the rate of change of the AMF. In particular, the eddy current and resultant tissue heating following the expressions:

(1) $I_{eddy} \propto dB/dT$
(2) Tissue Heating $\propto I_{eddy}^2$.

From the relationships (1) and (2), it is evident that reducing the rate of change of the AMF yields a significant reduction in tissue heating. In one embodiment of the present invention, this relationship is exploited by using a symmetrical triangular wave, as shown in FIG. 4b, as the fundamental waveform. By avoiding the high rates of change that occur as a sinusoid crosses the X-axis (FIG. 4a), and substituting the constant but lower rate of change associated with a triangular waveform (FIG. 4b), tissue heating may be reduced with little or no sacrifice in bioprobe heating. A triangular waveform, as shown in FIG. 4b, may be achieved by using an appropriate generator, such as a linear amplifier-based generator. Some distortion of the triangle is inevitable, but tangible reductions in tissue heating result from even small reductions in dB/dT.

The heating of both the tissue and the bioprobes increase with increased AMF amplitude. At low AMF amplitudes, small increases yield significant increases in magnetic heating. As the bioprobes approach saturation however, their relationship with the AMF amplitude becomes one of diminishing return. This relationship is unique to the particular magnetic material, as are the values that constitute "low" or "saturating" AMF amplitudes. Bioprobe heating is at first related to the AMF amplitude by an exponent >1, which gradually diminishes to an exponent <1 as saturation is approached. At typical pulse widths and duty cycles, eddy current heating is directly related to duty cycle. The capability to pulse the generator output, as illustrated in FIG. 5a or 5b, allows the benefits of operating at higher AMF amplitudes while maintaining a constant reduced tissue heating by reducing the duty cycle.

It is desirable to apply the AMF to the treatment area 205 of the patient 105. Generating high peak amplitude AMF over a large area requires a very large AMF generator and exposes large amounts of healthy tissue to unnecessary eddy current heating. Without some way of directing the field to where it is useful, disease in the chest or trunk may only be practically treated by placing the patient within a large solenoid coil. This would expose most of the major organs to eddy current heating, which must then be monitored and the AMF adjusted so as not to overheat any part of a variety of tissue types. Each of these tissue types has a different rate of eddy current heating. The peak AMF strength would need to be reduced to protect those tissue types that experience the most extreme eddy current heating. If the varieties of exposed tissue are minimized, it is likely that the AMF strength can be increased, and thereby reducing the treatment time and increasing the efficacy. One method of confining the high peak amplitude AMF to treatment area 205 is by defining the lowest reluctance path of magnetic flux with high permeability magnetic material. This path is referred to as a magnetic circuit (102 in FIGS. 1 and 302 in FIG. 3). The magnetic circuit may be provided so that all or most of the magnetic flux produced by the coil 322 may be directed to the treatment area 205. One benefit of the magnetic circuit 302 is that the necessary amount of flux may be reduced since the amount of flux extending beyond the treatment area 205 is minimized. Reducing the required flux reduces the required size and power of the AMF generator, and minimizes exposure of tissue outside the treatment area 205 to high peak amplitude AMF. In addition, a reduced area of AMF exposure avoids the unintentional heating of surgical or dental implants and reduces the likelihood that they will need to be removed prior to treatment, thereby avoiding invasive medical procedures. Concentrating the field permits the treatment of large volumes within the chest or trunk with a portable size device.

The material used to fabricate the magnetic circuit 302 may be appropriate to the peak amplitude and frequency of the AMF. The material may be, but is not limited to, iron, powdered iron, assorted magnetic alloys in solid or laminated configurations and ferrites. The pole faces 104, 204, and 304 may be shaped and sized to further concentrate the flux produced in the treatment area. The pole faces 304 may be detachable. Different pole pieces having different sizes and shapes may be used, so that the treatment area and volume may be adjusted. When passing from one material to another, the lines of magnetic flux 312 travel in a direction normal to the plane of the interface plane. Thus, the face 304 may be shaped to influence the flux path through gap 333. The pole faces 304 may be detachable and may be chosen to extend the magnetic circuit 302 as much as possible, to minimize gap the 333 while leaving sufficient space to receive that portion of the patient being treated. As discussed above, the addition of secondary coils can aid in the concentration of the field as well as reducing the field strength in sensitive areas.

Figure 6:
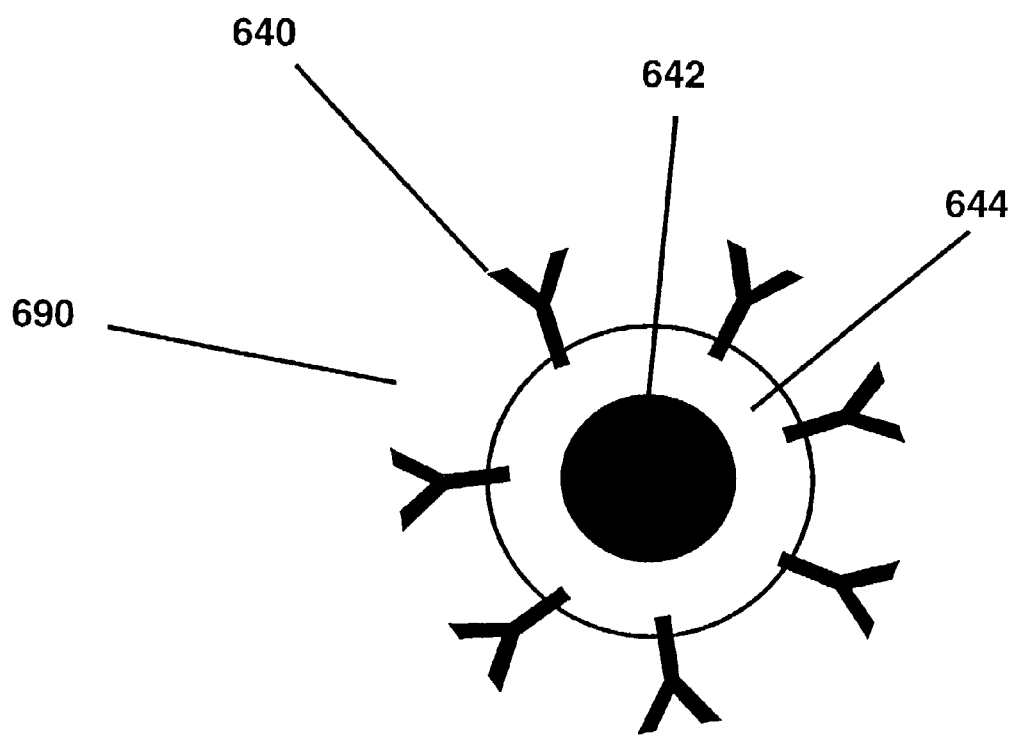
FIG. 6 schematically illustrates a thermotherapeutic bioprobe configuration according to an embodiment of the present invention.

FIG. 6 discloses a bioprobe configuration according to an embodiment of the present invention. A spherical shaped bioprobe 690, having a magnetic particle 642 at its center, is shown. The magnetic particle 642 may be covered with a coating 644. At least one targeting ligand 640, such as, but not limited to, an antibody, may be located on an exterior portion of the bioprobe 690. The targeting ligand 640 may be selected to seek out and bond with a particular type of cell or disease matter. Heat is generated when the magnetic particle 642 of the bioprobe 690 is subjected to the AMF. In a general sense, this heat represents an energy loss as the magnetic properties of the material are forced to oscillate in response to the applied alternating magnetic field. The amount of heat generated per cycle of magnetic field and the mechanism responsible for the energy loss depend on the specific characteristics of both the magnetic material of the particle 642 and the magnetic field. The magnetic particle 642 heats to a unique temperature, known as the Curie temperature, when subjected to the AMF. The Curie temperature is the temperature of the reversible ferromagnetic to paramagnetic transition of the magnetic material. Below this temperature, the magnetic material heats in an applied AMF. However, above the Curie temperature, the magnetic material becomes paramagnetic and its magnetic domains become unresponsive to the AMF. Thus, the material does not generate heat when exposed to the AMF above the Curie temperature. As the material cools to a temperature below the Curie temperature, it recovers its magnetic properties and resumes heating, as long as the AMF remains present. This cycle may be repeated continuously during exposure to the AMF. Thus, magnetic materials are able to self-regulate the temperature of heating. The temperature to which the particle 642 heats is dependent upon, inter alia, the magnetic properties of the material, characteristics of the magnetic field, and the cooling capacity of the target site 214. Selection of the magnetic material and AMF characteristics may be tailored to optimize treatment efficacy of a particular tissue or target type. In an embodiment of the present invention, the magnetic material may be selected to possess a Curie temperature between 40° C. and 150° C.

The magnetic attributes of ferromagnets, ferrites (ferrimagnets), and superparamagnets are determined by an ensemble of interacting magnetic moments in a crystalline structure. The magnetic moments of ferromagnets are parallel and equal in magnitude, giving the material a net magnetization, or net magnetization vector. By contrast, ferrites are ferrimagnetic, where adjacent magnetic moments are parallel in direction and unequal in magnitude, yielding a net magnetization in ferrimagnetic coupling. Superparamagnets possess clusters or collections of atomic magnetic moments that are either ferromagnetic or ferrimagnetic, however there may be no particular relationship in the orientation of the moments among several clusters. Thus, a superparamagnetic material may possess a net magnetic moment.

A magnetic domain may be defined as an area of locally saturated magnetization, and the magnetic domain boundary thickness, or the distance separating adjacent magnetic domains, may be about 100 nm. Thus, magnetic particles (ferromagnetic or ferrimagnetic) possessing a dimension smaller than 250 nm, and preferably less than about 100 nm, are single domain magnetic particles, where each particle is a magnetic dipole.

The mechanisms responsible for energy loss exhibited by single domain particles exposed to an alternating magnetic field are still not well understood, however a currently accepted description exists, which is included herein for clarity. When a single domain particle is exposed to an AMF, the whole magnetic dipole rotates in response to the field with a concomitant energy loss liberated as heat. This mechanism is often referred to as the Neél mechanism. The external magnetic forces required for this intrinsic change in magnetization depend upon the anisotropy energy of the magnetic domain, size, and shape of the single domain particle. Furthermore, it is currently accepted that there is a mechanical rotation of the entire single domain particle when exposed to an alternating magnetic field. This latter phenomenon, commonly called the Brownian mechanism, also contributes to the energy loss of a single domain particle, and is proportional to the viscosity of the material surrounding the particle. Thus, the coating 644 may enhance the heating properties of the bioprobe 690, particularly if the coating has a high viscosity, for example, if the coating is a polymer.

The heating mechanism responsible for the energy loss experienced by a single domain particle in an AMF can be clearly distinguished from the hysteresis heating of larger, or multidomain magnetic particles. Single domain particles of a given composition can produce substantially more heat per unit mass than multi-domain particles that are 1000 times larger (multi domain particles). The heating mechanism exhibited by single domain particles may be optimized to produce superior heating properties over larger particles for disease treatment. The amount of heat delivered to a cell may be tailored by controlling both the particle size and coating variation, as well as characteristics of the magnetic field, thereby providing a range of possible bioprobe compositions designed for material-specific treatments.

Many aspects of the magnetic particle 642, such as material composition, size, and shape, directly affect heating properties. Many of these characteristics may be designed simultaneously to tailor the heating properties for a particular set of conditions found within a tissue type. For example, first considering the magnetic particle 642, the most desirable size range depends upon the particular application and on the material(s) comprising the magnetic particle 642.

The size of the magnetic particle 642 determines the total size of the bioprobe 690. Bioprobes 690 that are to be injected may be spherical and may be required to have a long residence time in the bloodstream, i.e., avoid sequestration by the liver and other non-targeted organs. The bioprobe 690 may be successful in avoiding sequestration if its total diameter is less than about 30 nm. If the bioprobe 690 contains a magnetite ($Fe_3O_4$) particle 642, then a preferred diameter of the magnetic particle 642 may be between about 8 nm and about 20 nm. In this case, the bioprobes 690 may be sufficiently small to evade the liver, and yet the magnetic particle 642 still retains a sufficient magnetic moment for heating. Magnetite particles larger than about 8 nm generally tend to be ferrimagnetic and thus appropriate for disease treatment. If other elements, such as cobalt, are added to the magnetite, this size range can be smaller. This results directly from the fact that cobalt generally possesses a larger magnetic moment than magnetite, which contributes to the overall magnetic moment of the cobalt-containing magnetic particle 642. In general, the preferred size of the bioprobe 690 may be about 0.1 nm to about 250 nm, depending upon the disease indication and bioprobe composition.

While determining the size of the magnetic particle 642, its material composition may be determined based on the particular target. Because the self-limiting temperature of a magnetic material, or the Curie temperature, is directly related to the material composition, as is the total heat delivered, magnetic particle compositions may be tuned to different tissue or target types. This may be required because each target type, given its composition and location within the body, possesses unique heating and cooling capacities. For example, a tumor located within a region that is poorly supplied by blood and located within a relatively insulating region may require a lower Curie temperature material than a tumor that is located near a major blood vessel. Targets that are in the bloodstream will require different Curie temperature materials as well. Thus, in addition to magnetite, particle compositions may contain elements such as cobalt, iron, rare earth metals, etc.

The presence of the coating 644 and the composition of the coating material may form an integral part of the energy loss, and thus the heat produced, by the bioprobes 690. In addition, the coating 644 surrounding the particles may serve additional purposes. Its most important role may be to provide a biocompatible layer separating the magnetic material from the immunologic defenses in a patient, thereby controlling the residence time of the particles in the blood or tissue fluids.

For example, this control of residence time allows one to choose targeting ligands 640 that are best suited for a particular tissue type. In addition, the coating 644 may serve to protect the patient from potentially toxic elements in the magnetic particle 642. A second function of the coating materials may be the prevention of particle aggregation, as the bioprobes 690 may be suspended in a fluid. It may be also be advantageous to coat the bioprobe 690 with a biocompatible coating that is biodegradable. In such an application, both the coating 644 and the magnetic particle 642 may be digested and absorbed by the body.

Suitable materials for the coating 644 include synthetic and biological polymers, copolymers and polymer blends, and inorganic materials. Polymer materials may include various combinations of polymers of acrylates, siloxanes, styrenes, acetates, akylene glycols, alkylenes, alkylene oxides, parylenes, lactic acid, and glycolic acid. Further suitable coating materials include a hydrogel polymer, a histidine-containing polymer, and a combination of a hydrogel polymer and a histidine-containing polymer.

Coating materials may include combinations of biological materials such as a polysaccharide, a polyaminoacid, a protein, a lipid, a glycerol, and a fatty acid. Other biological materials for use as a coating material may be a heparin, heparin sulfate, chondroitin sulfate, chitin, chitosan, cellulose, dextran, alginate, starch, carbohydrate, and glycosaminoglycan. Proteins may include an extracellular matrix protein, proteoglycan, glycoprotein, albumin, peptide, and gelatin. These materials may also be used in combination with any suitable synthetic polymer material.

Inorganic coating materials may include any combination of a metal, a metal alloy, and a ceramic. Examples of ceramic materials may include a hydroxyapatite, silicon carbide, carboxylate, sulfonate, phosphate, ferrite, phosphonate, and oxides of Group IV elements of the Periodic Table of Elements. These materials may form a composite coating that also contains any biological or synthetic polymer. Where the magnetic particle 642 is formed from a magnetic material that is biocompatible, the surface of the particle itself operates as the biocompatible coating.

The coating material may also serve to facilitate transport of the bioprobe 690 into a cell, a process known as transfection. Such coating materials, known as transfection agents, include vectors, prions, polyaminoacids, cationic liposomes, amphiphiles, and non-liposomal lipids or any combination thereof. A suitable vector may be a plasmid, a virus, a phage, a viron, a viral coat. The bioprobe coating may be a composite of any combination of transfection agent with organic and inorganic materials, such that the particular combination may be tailored for a particular type of a disease material and a specific location within a patient's body.

To ensure that the bioprobe 690 selectively attaches to the target, an appropriate ligand 640 may be combined with the bioprobe 690. The association of a ligand or ligands with the bioprobes 690 allows for targeting of cancer or disease markers on cells. It also allows for targeting biological matter in the patient The term ligand relates to compounds which may target molecules including, for example, proteins, peptides, antibodies, antibody fragments, saccharides, carbohydrates, glycans, cytokines, chemokines, nucleotides, lectins, lipids, receptors, steroids, neurotransmitters, Cluster Designation/Differentiation (CD) markers, and imprinted polymers and the like. The preferred protein ligands include, for example, cell surface proteins, membrane proteins, proteoglycans, glycoproteins, peptides and the like. The preferred nucleotide ligands include, for example, complete nucleotides, complimentary nucleotides, and nucleotide fragments. The preferred lipid ligands include, for example phospholipids, glycolipids, and the like. The ligand 640 may be covalently bonded to or physically interacted with the magnetic particle 642 or the coating 644. The ligand 640 may be bound covalently or by physical interaction directly to an uncoated portion of the magnetic particle 642. The ligand 640 may be bound covalently or by physical interaction directly to an uncoated portion of the magnetic particle 642 and partially covered by the coating 644. The ligand 640 may be bound covalently or by physical interaction to a coated portion of the bioprobe 690. The ligand 640 may be intercalated to the coated portion of the bioprobe 690.

Covalent bonding may be achieved with a linker molecule. The term "linker molecule," as used herein, refers to an agent that targets particular functional groups on the ligand 640 and on the magnetic particle 642 or the coating 644, and thus forms a covalent link between any two of these. Examples of functional groups used in linking reactions include amines, sulfhydryls, carbohydrates, carboxyls, hydroxyls and the like. The linking agent may be a homobifunctional or heterobifunctional crosslinking reagent, for example, carbodiimides, sulfo-NHS esters linkers and the like. The linking agent may also be an aldehyde crosslinking reagent such as glutaraldehyde. The linking agent may be chosen to link the ligand 640 to the magnetic particle 642 or the coating 644 in a preferable orientation, specifically with the active region of the ligand 640 available for targeting. Physical interaction does not require the linking molecule and the ligand 640 be bound directly to the magnetic particle 642 or to the coating 644 by non-covalent means such as, for example, absorption, adsorption, or intercalation.

Figure 7:
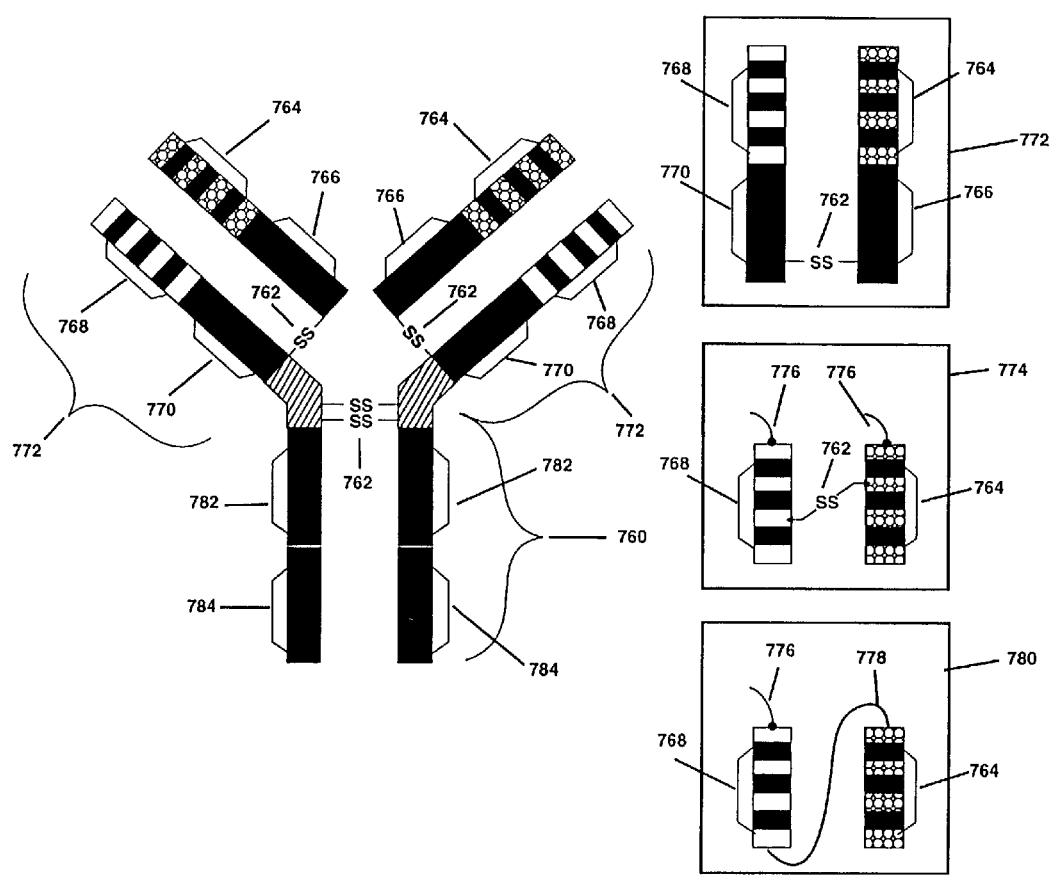
FIG. 7 schematically illustrates a disease specific targeting ligand component of a bioprobe according to an embodiment of the present invention.

FIG. 7 schematically shows an example of a ligand that may be used with an embodiment of the present invention. The ligand may be an antibody having a fragment crystallization (Fc) region 760 and fragment antigen binding (Fab) regions 772. The Fab regions 772 may be the antigen binding regions of the antibody that include a variable light region 764 and a constant light region 766 along with a variable heavy region 768 and a constant heavy region 770. Biological activity of antibodies may be determined to a large extent by the Fc region 760 of the antibody molecule. The Fc region may include complement activation constant heavy chains 782 and macrophage binding constant heavy chains 784. The Fe region 760 and Fab regions 772 may be connected by several disulfide linkages 762. Ligands that do not include the Fc region 760 may be preferable in order to avoid immunogenic response. Examples of these ligands may include antibody fragments such as, fragment antigen binding fragments (Fabs) 772, disulfide-stabilized variable region fragments (dsFVs) 774, single chain variable region fragments (scFVs) 780, recombinant single chain antibody fragments, and peptides.

An antigen binding fragment (Fab) 772 may include a single Fab region 772 of an antibody. A single Fab region may include a variable light 764 and a constant light region 766 bound to a variable heavy 768 and a constant heavy region 770 by a disulfide bond 762.

A disulfide-stabilized variable region fragment (dsFV) 774 may include a variable heavy region 768 and a variable light region 764 of antibody joined by a disulfide bond. A leader sequence 776, which may be a peptide, may be linked to the variable light 764 and variable heavy regions 768.

A single chain variable region fragment (scFV) 780 may include a variable heavy region 768 and variable light region 764 of antibody joined by a linker peptide 778. A leader sequence 776 may be linked to the variable heavy region 768.

A preferred ligand embodiment may include, for example, polyclonal antibodies, monoclonal antibodies, chimeric antibodies, humanized antibodies, human antibodies, recombinant antibodies, bispecific antibodies, antibody fragments, scFVs 780, Fabs 772, dsFVs 774, recombinant single chain antibody fragments, peptides, and the like. Bispecific antibodies are non-natural antibodies that bind two different epitopes that are typically chosen on two different antigens. A bispecific antibody is typically comprised of two different fragment antigen binding regions (Fabs) 772. A bispecific antibody may be formed by cleaving an antibody into two halves by cleaving the disulfide bonds 762 in the Fc region 782 only. Two antibody halves with different Fab regions 772 are then combined to form a bispecific antibody with the typical "Y" structure. One or more ligands can be present in the bioprobe formulation. Antibodies of virtually any origin may be used according to this embodiment, provided they bind the target, although human, chimeric, and humanized antibodies may aid in avoiding the patient's immunogenic response.

In another embodiment, the ligand 640 may be designed to target a specific cancer cell marker or markers. The particular cancer cell marker and ligand(s) 640 may be specific to, but not limited to, the type and location of the cancer such as, for example, tumors, metastatic cancer, minimal residual disease and the like. The ligand(s) 640 may have an affinity for the cancer marker or markers of interest. The cancer marker or markers may be selected such that they represent a viable target on the cancer cells of interest. The preferred cancer marker may be expressed on the surface of the cancer cells and is preferably present in very low amounts or not at all in normal cells. The preferred cancer marker may not be readily shed from the surface, or if shed, the ligand on the bioprobe may recognize a particular epitope of the marker that remains on the cell surface.

Figure 8:
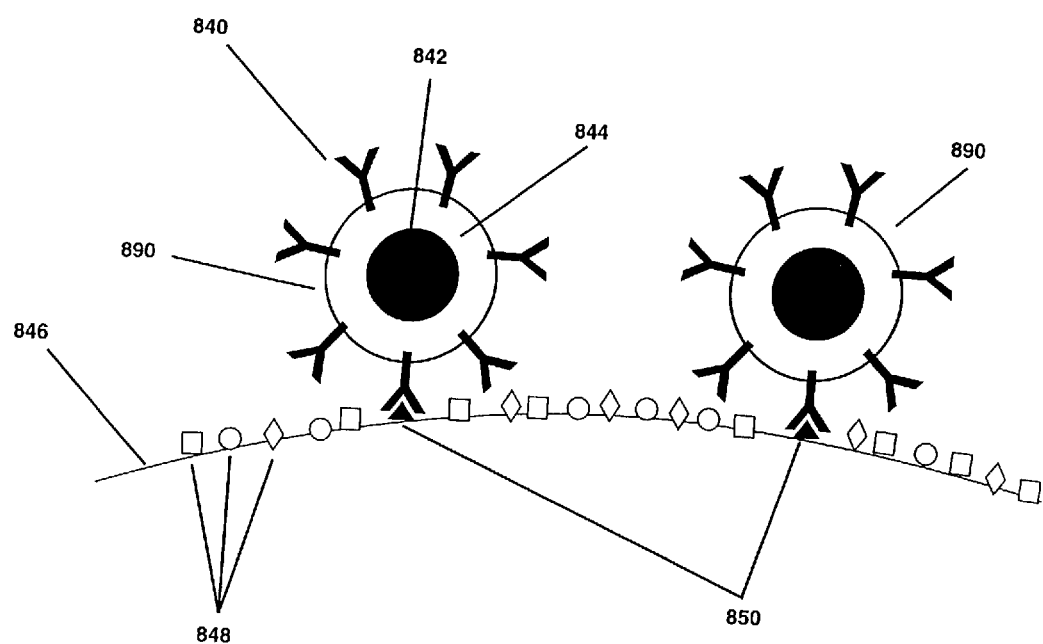
FIG. 8 schematically illustrates disease specific bioprobes bound to a disease cell surface according to an embodiment of the present invention.

FIG. 8 discloses an embodiment of the present invention wherein the bioprobes 890 include a magnetic particle 842 and a coating material 844 and are bound to the cell surface (wall) 846 by the ligand 840. The cell wall 846 may express several types of chemical species 848 and 850 that may serve as markers. The specificity of the bioprobes 890 may be represented by attachment to the targeted cell marker 850 over the many other markers or molecules 848 on the cell surface 846. One or more bioprobes may be attached to the cell surface 846 via the ligand 840. The ligands 840 may be adapted and the bioprobes 890 may be designed such that the bioprobes 890 remain on the cell surface 846 or they may be internalized into the cell. Once bound to the cell surface 846, the magnetic particle 842 of the bioprobe 890 heats in response to the AMF. The heat may emanate through the coating material 844 or through interstitial regions via convection, conduction, radiation, or any combination of these heat transfer mechanisms to the cell surface 846. The heated cell surface 846 becomes damaged, preferably in a manner that causes irreparable damage to the cell. When a bioprobe(s) 890 becomes internalized within the cell, the bioprobe heats the cell internally via convection, conduction, radiation, or any combination of these heat transfer mechanisms. When a sufficient amount of heat is transferred by the bioprobes 890 to the cell, the cell dies by necrosis, apoptosis or another mechanism.

The choice of a marker (antigen) 850 may be important to therapy utilizing bioprobes. For breast cancer and its metastases, a specific marker or markers may be chosen from cell surface markers such as, for example, members of the MUC-type mucin family, an epithelial growth factor (EGFR) receptor, a carcinoembryonic antigen (CEA), a human carcinoma antigen, a vascular endothelial growth factor (VEGF) antigen, a melanoma antigen (MAGE) gene, family antigen, a T/Tn antigen, a hormone receptor, growth factor receptors, a cluster designation/differentiation (CD) antigen, a tumor suppressor gene, a cell cycle regulator, an oncogene, an oncogene receptor, a proliferation marker, an adhesion molecule, a proteinase involved in degradation of extracellular matrix, a malignant transformation related factor, an apoptosis related factor, a human carcinoma antigen, glycoprotein antigens, DF3, 4F2, MGFM antigens, breast tumor antigen CA 15-3, calponin, cathepsin, CD31 antigen, proliferating cell nuclear antigen 10 (PC 10), and pS2.

For other forms of cancer and their metastases, a specific marker or markers may be chosen from cell surface markers such as, for example, a member of vascular endothelial growth factor receptor (VEGFR) family, a member of carcinoembryonic antigen (CEA) family, a type of anti-idiotypic mAB, a type of ganglioside mimic, a member of cluster designation/differentiation antigens, a member of epidermal growth factor receptor (EGFR) family, a type of a cellular adhesion molecule, a member of MUC-type mucin family, a type of cancer antigen (CA), a type of a matrix metalloproteinase, a type of glycoprotein antigen, a type of melanoma associated antigen (MAA), a proteolytic enzyme, a calmodulin, a member of tumor necrosis factor (TNF) receptor family, a type of angiogenesis marker, a melanoma antigen recognized by T cells (MART) antigen, a member of melanoma antigen encoding gene (MAGE) family, a prostate membrane specific antigen (PMSA), a small cell lung carcinoma antigen (SCLCA), a T/Tn antigen, a hormone receptor, a tumor suppressor gene antigen, a cell cycle regulator antigen, an oncogene antigen, an oncogene receptor antigen, a proliferation marker, a proteinase involved in degradation of extracellular matrix, a malignant transformation related factor, an apoptosis-related factor, a type of human carcinoma antigen.

In an embodiment of the invention, a bioprobe may include ligand(s) targeting the MUC-1 receptor of the mucin family. In yet another embodiment, a bioprobe has ligand(s) targeting at least one of the EGFR family such as Her-1, Her-2, Her-3 and Her-4MUC-1 (Human epithelial mucin, CD277), is a high molecular weight, transmembrane mucin glycoprotein expressed by most glandular and epithelial cell lineages. In addition, MUC-1 has a large extracellular domain, portions of which may be shed into the bloodstream. MUC-1 may have a protective role, as its extracellular domain forms elongated rigid structures extending above other molecules on the cell. MUC-1 also plays a role in cell-cell and cell-substrate adhesion. MUC-1 is highly expressed in many human adenocarcinomas, including 80% of breast cancers, and is associated with poor prognosis. Mucin (MUC-1 and MUC-2) expression is associated with tumor invasiveness. MUC-1 and MUC-2 expression is associated with invasive ductal carcinoma of the breast. MUC-1 is also present at high levels on many mylomas. Different tissues/cells produce differing glycoforms of MUC-1. Glycosylation of MUC-1 in malignant cells is often altered compared to normal tissue. MUC-1 is considered a truly tumor specific antigen, although it is also found on normal cells, its aberrant glycosylation on tumors creates new epitopes for targeting. The extracellular domain of MUC-1 may be shed into the blood stream. The ligand may target the unshed remainder of the MUC-1 expressed on the cell surface.

Overexpression of growth factor receptors such as the EGFR family is indicated in tumors and has been associated with increased cell resistance to the cytotoxic effects of macrophages and cytotoxic factors, such as TNF (tumor necrosis factor), which can lead to tumor growth. The protein encoded by the Her-1/neu gene is a 170,000 Dalton protein, referred to as Her-1. The protein encoded by the Her-2/neu gene is a 185,000 Dalton protein referred to as Her-2. Both proteins have an intracellular domain, a transmembrane domain that includes two cysteine-rich repeat clusters, and an intracellular kinase domain. The extracellular domain of Her-2 may be shed into the bloodstream. Thus, the ligand may target the unshed remainder of the Her-2 expressed on the surface of the cell.

For ovarian cancers and their metastases, a specific marker or markers may be chosen from cell surface markers such as, for example, one of ERBB2 (Her-2) antigen and CD64 antigen. For ovarian and/or gastric cancers and their metastases, a specific marker or markers may be chosen from cell surface markers such as, for example, a polymorphic epithelial mucin (PEM). For ovarian cancers and their metastases, a specific marker or markers may be chosen from cell surface markers such as, for example, one of cancer antigen 125 (CA125) or matrix metalloproteinase 2 (MMP-2). For gastric cancers and their metastases, a specific marker or markers may be chosen from cell surface markers such as, for example, one of CA19-9 antigen and CA242 antigen.

For non-small-cell lung cancer (NSCLC), colorectal cancer (CRC) and their metastases, a specific marker or markers may be chosen from cell surface markers such as, for example, vascular endothelial growth factor receptor (VEGFR), anti-idiotypic mAb, and carcinoembryonic antigen (CEA) mimic. For at least one of small-cell lung cancer (SCLC), malignant melanoma, and their metastases, a specific marker or markers may be chosen from cell surface markers such as, for example, anti-idiotypic mAB or GD3 ganglioside mimic. For melanoma cancers and their metastases, a specific marker or markers may be chosen from cell surface markers such as, for example, a melanoma associated antigen (MAA). For small cell lung cancers and their metastases, a specific marker or markers may be chosen from cell surface markers such as, for example, a small cell lung carcinoma antigen (SCLCA).

For colorectal cancer (CRC) and/or locally advanced or metastatic head and/or neck cancer, a specific marker or markers may be chosen from cell surface markers such as, for example, epidermal growth factor receptor (EGFR). For Duke's colorectal cancer (CRC) and its metastases, a specific marker or markers may be chosen from cell surface markers such as, for example, Ep-CAM antigen.

For non-Hodgkin's lymphoma (NHL) and its metastases, a specific marker or markers may be chosen from cell surface markers such as, for example, cluster designation/differentiation(CD) 20 antigen or CD22 antigen. For B-cell chronic lymphocytic leukaemia and associated metastases, a specific marker or markers may be chosen from cell surface markers such as, for example, CD52 antigen. For acute myelogenous leukaemia and its metastases, a specific marker or markers may be chosen from cell surface markers such as, for example, CD33 antigen.

For prostate cancers and their metastases, a specific marker or markers may be chosen from cell surface markers such as, for example, prostate membrane specific antigen (PMSA). For carcinomatous meningitis and their metastases, a specific marker or markers may be chosen from cell surface markers such as, for example, one of a vascular endothelial growth factor receptor (VEGFR) or an epithelial associated glycoprotein, for example, HMFGI (human milk fat globulin) antigen.

For lung, ovarian, colon, and melanoma cancers and their metastases, a specific marker or markers may be chosen from cell surface markers such as, for example, B7-H1 protein. For colon, breast, lung, stomach, cervix, and uterine cancers and their metastases, a specific marker or markers may be chosen from cell surface markers such as, for example, TRAIL Receptor-1 protein, a member of the tumor necrosis factor receptor family of proteins. For ovarian, pancreatic, non-small cell lung, breast, and head and neck cancers and their metastases, a specific marker or markers may be chosen from cell surface markers such as, for example, EGFR (epidermal growth factor receptor).

For anti-angiogenesis targeting of tumor blood supply, a specific marker or markers may be chosen from cell surface markers such as, for example, Integrin $\alpha v \beta 3$, a cell surface marker specific to endothelial cells of growing blood vessels.

For targeting of colon and bladder cancer and their metastases, a specific marker or markers may be chosen from cell surface markers such as, for example, RAS, a signaling molecule that transmits signals from the external environment to the nucleus. A mutated form of RAS is found in many cancers.

In another embodiment, the ligand 640 may be targeted to a predetermined target associated with a disease of the patient's immune system. The particular target and ligand(s) 640 may be specific to, but not limited to, the type of the immune disease. The ligand(s) 640 may have an affinity for a cell marker or markers of interest. The marker or markers may be selected such that they represent a viable target on T cells or B cells of the patient's immune system. The ligand(s) 640 may have an affinity for a target associated with a disease of the patient's immune system such as, for example, a protein, a cytokine, a chemokine, an infectious organism, and the like.

For diseases of the patient's immune system, a specific marker or markers may be chosen from cell surface markers. The targeted cells may be T or B cells of the immune system. For rheumatoid arthritis, a specific marker or markers may be chosen from cell surface markers such as, for example, one of CD52 antigen, tumor necrosis factor (TNF), and CD25 antigen. For rheumatoid arthritis and/or vasculitis, a specific marker or markers may be chosen from cell surface markers such as, for example, CD4 antigen. For vasculitis, a specific marker or markers may be chosen from cell surface markers such as, for example, CD18 antigen. For multiple sclerosis, a specific marker or markers may be chosen from cell surface markers such as, for example, CD52 antigen.

In another embodiment, the ligand 640 may be targeted to a predetermined target associated with a pathogen-borne condition. The particular target and ligand(s) 640 may be specific to, but not limited to, the type of the pathogen-borne condition. A pathogen is defined as any disease-producing agent such as, for example, a bacterium, a virus, a microorganism, a fungus, and a parasite. The ligand(s) 640 may have an affinity for the pathogen or pathogen associated matter. The ligand(s) 640 may have an affinity for a cell marker or markers associated with a pathogen-borne condition. The marker or markers may be selected such that they represent a viable target on infected cells.

For a pathogen-borne condition, the ligand(s) 640 for therapy utilizing bioprobes may be chosen to target the pathogen itself. For a bacterial condition, a predetermined target may be the bacteria itself, for example, one of *Escherichia coli* or *Bacillus anthracis*. For a viral condition, a predetermined target may be the virus itself, for example, one of Cytomegalovirus (CMV), Epstein-Barr virus (EBV), a hepatitis virus, such as Hepatitis B virus, human immunodeficiency virus, such as HIV, HIV-1, or HIV-2, or a herpes virus, such as Herpes virus 6. For a parasitic condition, a predetermined target may be the parasite itself, for example, one of *Trypanasoma cruzi*, Kinetoplastid, *Schistosoma mansoni, Schistosoma japonicum* or *Schistosoma brucei*. For a fungal condition, a predetermined target may be the fungus itself, for example, one of Aspergillus, *Cryptococcus neoformans* or Rhizomucor.

For a pathogen-borne condition, the ligand(s) 640 for therapy utilizing bioprobes may be chosen to target cell markers of pathogen infected cells. For the HIV virus, the predetermined target may be CTLA4 expressed on the surface of HIV infected T cells. CTLA4 migrates to the infected cell's outer surface when the HIV virus is ready to be released.

In another embodiment, the ligand 640 may be targeted to a predetermined target associated with undesirable material. The particular target and ligand(s) 640 may be specific to, but not limited to, the type of the undesirable material. Undesirable material is material associated with a disease or an undesirable condition, but which may also be present in a normal condition. For example, the undesirable material may be present at elevated concentrations or otherwise be altered in the disease or undesirable state. The ligand(s) 640 may have an affinity for the undesirable target or for biological molecular pathways related to the undesirable target. The ligand(s) 640 may have an affinity for a cell marker or markers associated with the undesirable material.

For an undesirable material, the ligand(s) 640 may be chosen to target biological matter associated with a disease or undesirable condition. For arteriosclerosis, a predetermined target may be, for example, apolipoprotein B on low density lipoprotein (LDL). An undesirable material may be adipose tissue or cellulite associated with obesity or a precursor to obesity. A predetermined marker or markers for obesity maybe chosen from cell surface markers such as, for example, one of gastric inhibitory polypeptide receptor and CD36 antigen. Another undesirable predetermined target may be clotted blood.

In another embodiment, the ligand 640 may be targeted to a predetermined target associated with a reaction to an organ transplanted into the patient. The particular target and ligand (s) 640 may be specific to, but not limited to, the type of organ transplant. The ligand(s) 640 may have an affinity for a biological molecule associated with a reaction to an organ transplant. The ligand(s) 640 may have an affinity for a cell marker or markers associated with a reaction to an organ transplant. The marker or markers may be selected such that they represent a viable target on T cells or B cells of the patient's immune system.

For reaction to a transplanted organ, the ligand(s) 640 may be chosen to target the immune response to a transplant. The transplanted organ may be treated before or after transplantation. For kidney transplantation, a predetermined marker or markers may be chosen from cell surface markers such as, for example, human T cell receptor (CD3) antigen or CD18 antigen. For kidney and bone marrow transplantation, a predetermined marker or markers may be chosen from cell surface markers such as, for example, CD52 antigen. For liver and bone marrow transplantation, a predetermined marker or markers may be chosen from cell surface markers such as, for example, one of CD154 antigen and CD8 antigen. For transplantation tolerance, a predetermined marker or markers may be chosen from cell surface markers such as, for example, CD4. For bone marrow, a predetermined marker or markers may be chosen from cell surface markers such as, for example, CD52 antigen for efficient depletion of T cells from bone marrow before transplantation in order to avoid graft versus host disease. For xenotransplantation or xenografting, a predetermined marker or markers may be, for example, galactose.

Galactose is known to be on pig organs, but is not present in humans. In another embodiment, the ligand 640 may be targeted to a predetermined target associated with a toxin in the patient. A toxin is defined as any poison produced by an organism including, but not limited to, bacterial toxins, plant toxins, insect toxin, animal toxins, and man-made toxins. The particular target and ligand(s) 640 may be specific to, but not limited to, the type of toxin. The ligand(s) 640 may have an affinity for the toxin or a biological molecule associated with a reaction to the toxin. The ligand(s) 640 may have an affinity for a cell marker or markers associated with a reaction to the toxin.

For a toxin in the patient, the ligand(s) 640 may be chosen to target the toxin. A bacterial toxin target may be, for example, one of Cholera toxin, Diphtheria toxin, and Clostridium botulinus toxin. An insect toxin may be, for example, bee venom. An animal toxin may be, for example, snake toxin, for example, *Crotalus durissus terrificus* venom.

In another embodiment, the ligand 640 may be targeted to a predetermined target associated with a hormone-related disease. The particular target and ligand(s) 640 may be specific to, but not limited to, a particular hormone disease. The ligand(s) 640 may have an affinity for a hormone or a biological molecule associated with the hormone pathway. The ligand(s) 640 may have an affinity for a cell marker or markers associated with the hormone disease.

For a hormone related disease, the ligand(s) 640 may be chosen to a cell marker or markers. For estrogen-related disease or conditions, a predetermined target may be, for example, estrogen or cell surface marker or markers such as, for example, estrogen receptor. For human growth hormone disease, the predetermined target may be, for example, human growth hormone.

In another embodiment, the ligand 640 may be targeted to a predetermined target associated with non-cancerous disease material. The particular target and ligand(s) 640 may be specific to, but not limited to, a particular non-cancerous disease material. The ligand(s) 640 may have an affinity for a biological molecule associated with the non-cancerous disease material. The ligand(s) 640 may have an affinity for a cell marker or markers associated with the non-cancerous disease material.

For non-cancerous disease material, the ligand(s) 640 may be chosen to be a predetermined target such as, for example, one of non-cancerous diseased deposits and precursor deposits. For Alzheimer's disease, a predetermined target may be, for example, amyloid B protein and its deposits or apolipoprotein and its deposits.

In another embodiment, the ligand 640 may be targeted to a proteinaceous pathogen. The particular target and ligand(s) 640 may be specific to, but not limited to, a particular proteinaceous pathogen. The ligand(s) 640 may have an affinity for a proteinaceous pathogen or a biological molecule associated with the proteinaceous pathogen. The ligand(s) 640 may have an affinity for a cell marker or markers associated with the proteinaceous pathogen. For prion diseases also known as transmissible spongiform encephalopathies, a predetermined target may be, for example, Prion protein 3F4.

At least two approaches may be pursued for exposure of disease material to the bioprobe therapy: treatment within the patient (intracorporeal) and treatment external to the patient (extracorporeal). In extracorporeal hyperthermal therapy, bioprobes may be used to lyse, denature, or otherwise damage the disease material by removing material from the patient, exposing the material to AMF, and returning the material to the body. The bioprobes may be introduced into the patient's body and then removed from the patient along with the material that is being extracted. The bioprobes may be separated from the material being extracted after treatment. The bioprobes may also be introduced to the extracted material while the extracted material is outside of the patient's body. For example, where the extracted material is the patient's blood, the bioprobes may be introduced to the vascular circulating system or into the blood circulating outside of the body, prior to irradiation with the AMF.

For example, to target bioprobe/target complexes that are carried primarily in the blood serum or plasma, the blood serum or plasma may be extracorporeally separated from the other blood components, exposed to AMF to destroy the target, and recombined with the other blood components before returning the blood to the body. The bioprobes may be introduced into the vascular circulating system, the blood circulating outside of the body, or the blood serum or plasma after it is separated. In another embodiment, the bioprobes may be contained in a vessel or column through which the blood circulating outside of the body or the blood serum or plasma flows. The vessel or column may be exposed to AMF to destroy the targeted cells or antigens before returning the blood to the body. All of the indications described above may be targeted using either treatment within the patient (intracorporeal) and treatment external to the patient (extracorporeal).

A method of administering the bioprobes 890 to the desired area for treatment and the dosage may depend upon, but is not limited to, the type and location of the disease material. The size range of the bioprobes 890 allows for microfiltration for sterilization. An administration method may be, for example, wash, lavage, as a rinse with sponge, or other surgical cloth as a perisurgical administration technique. Other methods of administration may include intravascular injection, intravenous injection, intraperitoneal injection, subcutaneous injection, and intramuscular injection. The bioprobes 890 may be formulated in an injectable format (suspension, emulsion) in a medium such as, for example, water, saline, Ringer's solution, dextrose, albumin solution, and oils. The bioprobes may also be administered to the patient through topical application via a salve or lotion, transdermally through a patch, orally ingested as a pill or capsule or suspended in a liquid or rectally inserted in suppository form. Bioprobes may also be suspended in an aerosol or pre-aerosol formulation suitable for inhalation via the mouth or nose. Once administered to the patient, delivery of the bioprobes 890 to the target site may be assisted by an applied static magnetic field due to the magnetic nature of the bioprobes. Assisted delivery may depend on the location of the targeted cancer. The bioprobes may also be delivered to the patient using other methods. For example, the bioprobes may be administered to the patient orally, or may be administered rectally.

Another method of administering the bioprobes 890 to the desired area for treatment may include administering the magnetic material 642 composition and the ligand 640 to the patient separately and combining the ligand with the magnetic material in the patient's body. The ligand may be chosen to recognize a predetermined target. A ligand having a binder may be administered to the patient separately from the administration of a magnetic particle having a receptor to the binder. The ligand with the binding molecule may combine with the magnetic particle with receptor through the binder/receptor interaction in the patient's body to form a targeted bioprobe for therapy. In another embodiment, a ligand having a receptor may be administered to the patient separately from the administration of a magnetic particle having a binder. The ligand with the receptor may combine with the magnetic particle with the binding molecule through the binder/receptor interaction in the patient's body to form a targeted bioprobe for therapy.

In one approach, a ligand having a binder to a target molecule may be administered to the patient separately from the administration of a magnetic particle conjugated to a target molecule. The ligand having the binder may combine with the magnetic particle with the target molecule through an interaction between the binder and the target molecule in the patient's body to form a targeted bioprobe for therapy. The administration of the ligand separate from the magnetic particle may allow for higher doses of ligand or multiple doses of the ligand to be given to the patient and may allow for time for the ligand to localize at the predetermined target. The magnetic particle may then be added to combine with the ligand at an appropriate time before bioprobe therapy.

In another approach, a biotinylated ligand and an avidin, for example, streptavidin, conjugated magnetic particle may be administered to the body separately and at separate times. The biotinylated ligand and the avidin conjugated magnetic particle may combine in the patient's body prior to bioprobe therapy. Also, for example, a streptavidin conjugated ligand and a biotinylated magnetic particle may be administered to the body separately and at separate times. The streptavidin conjugated ligand and the biotinylated magnetic particle may combine in the patient's body prior to bioprobe therapy. For example, the ligand may be a fusion protein comprised of a target-binding fragment combined with streptavidin and the magnetic particle may be biotinylated. The ligand may be administered separately to the patient and the target-binding fragment may be designed for a predetermined target for bioprobe therapy. The biotinylated magnetic particle may be administered separately and combine with the streptavidin fusion protein in the patient's body.

Another method of administering the bioprobes 890 to the desired area for treatment may include administering the magnetic material 642 composition and the ligand 640 to the patient separately and combining the ligand with the magnetic material in the patient's body. A bispecific ligand may be administered to the patient separately from the administration of a magnetic particle conjugated to a target molecule. The bispecific ligand may be designed to recognize a predetermined target for therapy and also to recognize a target molecule. The bispecific ligand may combine with the magnetic particle conjugated to a target molecule in the patient's body to form a targeted bioprobe for therapy. For example, a bispecific antibody may be used to recognize the predetermined target and to also recognize streptavidin. The bispecific antibody and a streptavidin conjugated magnetic particle may be administered to the patient separately and at a separate time or times. The bispecific ligand may combine with the magnetic particle conjugated to strepatvidin through the affinity interactions in the patient's body to form a targeted bioprobe for therapy.

Once administered by any of the above methods, the movement of the bioprobes can be influenced by an AMF with a DC offset and a suitable gradient, or even by a simple DC magnetic field with a suitable gradient. The magnetic field pattern may also be influenced to separate the patient from an electric field component associated with the magnetic field to reduce an undesirable dielectric heating of patient tissue or cells.

Figure 9A:
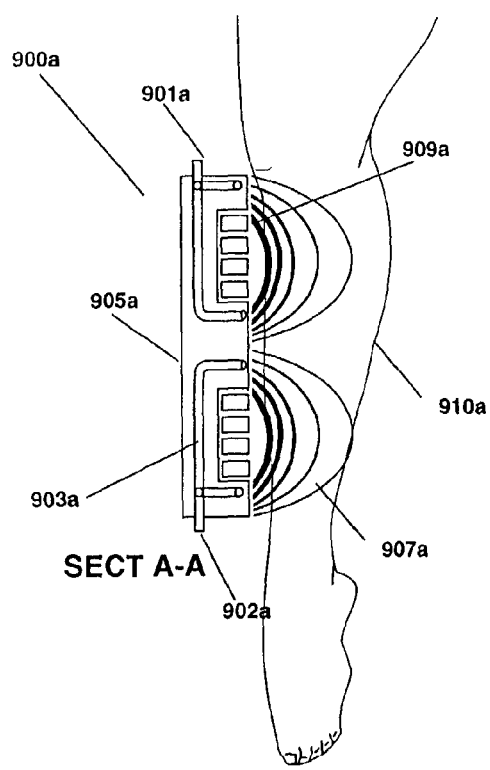
FIG. 9a schematically illustrates a thermotherapeutic treatment according to an embodiment of the present invention.
Figure 9B:
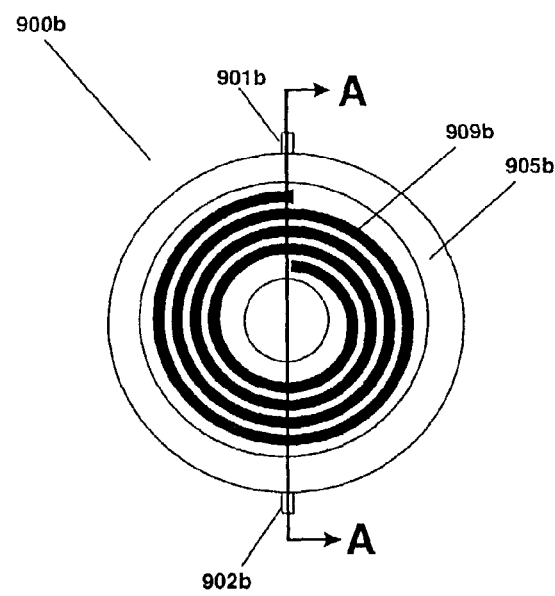

FIGS. 9a and 9b disclose a treatment device for carrying out the thermotherapeutic treatment according to another embodiment of the present invention. The treatment device illustrated in FIGS. 9a and 9b includes at least one pancake coil (909a and 909b) and a core (905a and 905b). The treatment device may also include a liquid cooling input (901a and 901b) output (902a and 902b), as well as a cooling circuit 903a. An AC current applied to the coil (909a and 909b), as described above, yields an AMF with a field shape approximated by the field lines 907a. The treatment device is applicable for treating areas close to the surface, for example, the skin or may be applied with sufficient magnetic field strength to treat the patient's muscle and bone tissue. The coil (909a and 909b) may be coated with an appropriate insulating material for placement directly on the skin of a patient. In FIG. 9a, the magnetic field generating device 900a is shown treating undesirable material along the patient's leg 910a. For treatment areas associated with target materials such as melanoma or cellulite, the apparatus applies sufficient field strength to kill undesirable material while limiting exposure to a non-targeted material.

FIG. 9b schematically illustrates a face of a magnetic generating device 900b. A cross sectional view of the coil illustrated in FIG. 9a is disclosed along axis A-A in FIG. 9b. The device 900b is shown provided with a core 905b and a coil 909b from which, in operation, the magnetic field lines emanate. When assembled, most of the magnetic field lines 907a, as illustrated in FIG. 9a, appear to be touching the leg 910a. The magnetic field will be most intense close to the coil 909a and will diminish exponentially as the distance from the coil 909a increases. This characteristic provides for high field strength in the tissue near the surface while minimizing the exposure of deeper tissues.

EXAMPLES

Having generally described the invention, a more complete understanding thereof may be obtained by reference to the following examples that are provided for purposes of illustration only and do not limit the invention.

Example 1

Identify Ferromagnetic Particles with Proper Curie Temperatures

For magnetic materials, the saturation magnetization ($4\pi M_s$) and the Curie temperatures ($T_c$) depend on the material composition. The Curie temperature of the material may lie in the range 40° C.–150° C., although it may also lie outside this range. For example, manganese alloys of the general formula $RMn_2X$, where R is a rare earth, such as La, Ce, Pr, or Nb, and X is either Ge or Si, exhibit $T_c$'s of 30–60° C. and may be used in bioprobes. Other oxides of ferrite, garnets, and spinels may be used as bioprobes. For example, substituting (doping) Gd and Al for Fe of $Y_3Fe_5O_{12}$ garnets provides control of both $T_c$ and $4\pi M_s$. These types of ferromagnetic media are commercially available from, for example, TRAK Ceramics, Hagerstown, Md.; Ceramic Magnetics, Fairfield, N.J.; and TMC Magnetics, Pine Brook, N.J. Sub-micron size particles may be produced through ball milling, solution-precipitation, or sol-gel processing of these materials.

The heating profile (temperature versus time) of the magnetic material may be determined under a variety of model conditions, for example, as suspensions in water, within cell culture media, agar gel, etc.

In general, a fundamental frequency of several MHz is effective for inductive heating. At such frequencies, however, tissue heating may be problematic. Another frequency range, which results in less tissue heating, is 100 kHz to 500 kHz.

Tissue heating places limitations on the practical amplitude of the magnetic field. A preferred range may be from 100 to 200 Oersteds (Oe), using a constant waveform generator. Difficulties may arise in achieving desired particle heating with many materials when the field falls in this range. The field conditions may also be inadequate because the number of bioprobes attaching to the targeted cells may often be unknown and/or limited by the specifics of cellular biology. The limitation may be overcome by using a pulsed generator and setting the field conditions, field amplitude and pulse characteristics, to levels that heats the bioprobes sufficiently to kill targeted cells without excessive peripheral tissue heating. Thus, under pulsed conditions, peak magnetic fields of up to a few thousand Oersteds (Oe) may be used.

Example 2

Synthesis of Bio-Compatible Coatings

The bioprobe particles selected during Example 1 may be coated with a biocompatible polymer according to a following embodiment of the procedure. Poly (methacrylic acid-co-hydroxyethylmethacrylate) as a biocompatible coating material for bioprobes may be synthesized from methacrylic acid and hydroxyethyl methacrylate using free-radical polymerization in the presence of the magnetic particles. To avoid aggregation of the magnetic nanometer sized particles during polymerization, the polymerization may be carried out in a microemulsion environment consisting of water/toluene/sodium bis-2-ethylhexyl sulfosuccinate. The sodium bis-2-ethylhexyl sulfosuccinate acts as an ionic surfactant to make a stabilizing layer around the magnetic particles. Methacrylic acid ($1.45 \times 10^{-2}$ moles), hydroxyethyl-methacrylate ($5.38 \times 10^{-4}$ moles), N,N'-methylene bisacrylamide ($8.12 \times 10^{-5}$ moles), and 2,2'-azobisbutyronitrile ($7.62 \times 10^{-5}$ moles) are added to a mixture of water/toluene/ bis-2-ethylhexyl sulfosuccinate (0.38/0.47/5.1×10$^{-2}$ moles) with magnetic particles. The polymerization may be carried out at 55° C. for several hours under nitrogen. Coated bioprobe particles may then be recovered by precipitation in an excess of acetone/ethanol followed by several washings. The coated bioprobe particles may be kept in vacuum overnight to remove residual monomers.

Example 3

Attachment of the Antibodies to the Particles

The attachment of the antibodies to the coated magnetic particles may be accomplished by use of a small "linker" molecule with differentiated terminals that permit covalent antibody attachment to the biocompatible polymer coating. Attachment occurs in the Fc region using the electrophilic C-terminal residue of the antibody to react with the nucleophilic portion of the linker. The other terminus of the linker may be activated by UV photolysis. The photoactive end of the linker may react with the polymer coating. Conjugation of the antibodies to the nanoparticles using this technique may proceed in the following manner. The antibody may be covalently conjugated to 4-[p-azidosalicylamido]butylamine (ASBA) using 1-ethyl-3-(3-dimethylaminopropyl)-carbodiimide, EDC. The EDC may activate the C-terminal carboxyl function, making it susceptible to attack by the primary amino group of the ASBA. The antibody, covalently tethered to the linker, may be subjected to photolysis in the presence of the polymer-coated nanoparticles. On exposure to UV, the azido function on the linked ASBA may generate a nitrene in-situ that covalently inserts into the polymer coat yielding a nanoparticle that may be covalently bound to the antibody through the linker.

If the selected magnetic nanoparticles are not toxic and do not require polymer coating, the antibodies may be attached to the nanoparticles directly. The immunoglobulin G's may be cleaved at the disulfide linkages connecting the two portions of the antibody and purified by chromatography. The fragments, containing residual sulfhydryl groups, may be conjugated directly to the metal clusters forming coordinate covalent linkages.

Example 4

Efficacy of bioprobes: In vitro Trials with MCF-7 Breast Cancer Cells

The bioprobes included 50-nm, $Fe_3O_4$ particles surrounded by a dextran shell, to which the monoclonal antibody (mAB) for Her-2 was covalently linked. The particles were suspended in cellular growth media including Modified Eagle's Medium (MEM) containing 10% fetal calf serum, insulin (10 µg/ml), fungizone, glutamine, penicillin, streptomycin, sodium pyruvate and non-essential amino acids, which was then added to cultures of MCF-7 cells. The MCF-7 cells represent an estrogen receptor-positive human breast carcinoma, and were grown on tissue culture inserts with a 10 mm diameter possessing porous frits with pore sizes of 0.02 or 0.2 µm.

The alternating magnetic field source was an industrial 3.5 kW variable duty radio-frequency generator with a frequency of 740 kHz and time-averaged field amplitude of 500 Oe (peak field amplitude, 1300 Oe). The generator produced pulses with a length of 4.174 ms, at a pulse repetition rate of 121 Hz, to give a duty cycle of 50.6%. The generator provided power to a 14-mm (inner diameter), 5-turn copper solenoid coil into which sample containers were inserted. The average temperature of the media in all samples monitored in situ using silicon dioxide temperature probes resistant to electromagnetic (EM) fields obtained from FISO Technologies Inc., Ste-Foy, Quebec, Canada.

A series of water bath tests was conducted to determine the hyperthermia tolerance of the cell cultures. The purpose of these tests was to obtain "positive control" data on the effects of hyperthermia on the cancer cell cultures and to aid in the interpretation of experiments using the bioprobe system. Exposing cellular culture media to an alternating magnetic field, without the presence of the bioprobes, may cause some tissue heating. Such magnetic induction heating is determined by the frequency and field strength of the magnetic field. Thus, to avoid overheating the media with the applied magnetic field, water bath tests were conducted to provide threshold limits of magnetic induction heating of the media containing cells not receiving the treatment. Table 1 lists results of cell death fraction as a function of exposed temperature and exposure time. The MCF-7 cell line is shown to be unaffected by heat exposure to 42° C. for 30 minutes. Thus, for all in vitro experiments, the magnetic field strengths were fixed at levels where the average temperature of the cellular growth media (containing no cells or magnetic fluid) remained at or below 42° C.

TABLE 1

Result of water bath tests with MCF-7 cells.

| Temperature (° C.) | Time of exposure (min.) | % dead cells |
|---|---|---|
| 37* | N/A | 4 |
| 42 | 30 | 4 |
| 43 | 15 | 5 |
| 46 | 5 | 92 |

*Represents a control cell culture sample not placed into water bath.

Cells intended for treatment were combined with bioprobes containing the Her-2 antibody and incubated for 8 minutes at 20° C., followed by three rinses with growth media, to remove unattached bioprobes. The cell cultures were analyzed before and 6 hours after the 20-minute treatments with the alternating magnetic field (AMF). The fraction of dead cells for the targeted sample (T1) and control samples (C1-C3) are presented in Table 2. In the targeted sample, 91%±5% (n=7) of the MCF-7 cells were killed. Of the cells killed, about 70% cells were be lysed by the treatment, as measured by spectrophotometric analysis of cytoplasmic lactate dehydrogenase (LDH), an enzyme produced by living cells. The remaining approximately 20% underwent apoptosis, as measured using a commercial fluorescent apoptosis-staining assay. The kill rates for the targeted cells are significantly higher than baseline death and apoptotic rates of 4%±1% in all controls (Table 2). Control groups include: 1) cells receiving no exposure to either the AMF or bioprobes (Sample C1); 2) cells exposed to the bioprobes alone (Sample C2); and 3) cells exposed to the AMF alone (Sample C3). Similar baseline deaths of all controls confirm that neither the AMF alone, nor only the presence of the bioprobes, is toxic to the cells. Higher than normal cell death occurs only when the AMF is applied after the bioprobes have attached to a cell.

TABLE 2

In Vitro Results with MCF-7 Cells.

| SAMPLE | TREATMENT | % DEAD CELLS (N = 7) |
|---|---|---|
| C1 | NO BIOPROBES, NO AMF | 4 ± 1 |
| C2 | BIOPROBES, NO AMF | 5 ± 1 |
| C3 | NO BIOPROBES; AMF | 4 ± 1 |
| T1 | BIOPROBES WITH AMF | 91 ± 5 |

Example 5

Selectivity of Bioprobes: In vitro Trials with SK-CO-1 Colon Cancer Cells

For the in vitro studies, the MCF-7 human breast cancer cells were chosen because their Her-2 expression was sufficient for detection, but was not expressed in extraordinarily high amounts as is the case with the more aggressive MDA-MB-231 (human breast carcinoma cells known to significantly over express Her-2) cell line. As a control, cultures of SK-CO-1 cells (human colon adenocarcinoma cells known to be Her-2 negative) were chosen to provide a reasonable model to challenge the effectiveness and selectivity of the bioprobe system.

To investigate the selectivity of the bioprobes, SK-CO-1 human colon cancer cells known to be Her-2 negative were treated in the same manner. For this group, rates of apoptosis were 13% for cells treated with an alternating magnetic field (AMF) and bioprobes, 18% for cells receiving no AMF and no bioprobes (represents normal death rate), 10% for cells exposed only to an AMF, and 8% for cells exposed to only bioprobes. These results are summarized in Table 3. Thus, no significant differences were seen in the death rates of SK-CO-1 cells when used with any or all components of the invention, demonstrating selective tumoricidal activity for the MCF-7 breast cells.

TABLE 3

In Vitro Results with SK-CO-1 Cells.

| SAMPLE | TREATMENT | % DEAD CELLS |
|---|---|---|
| SK-CO-1 | NO BIOPROBES, NO AMF | 18 |
| SK-CO-1 | BIOPROBES, NO AMF | 8 |
| SK-CO-1 | NO BIOPROBES; AMF | 13 |
| T1 (MCF-7) | BIOPROBES WITH AMF | 91 ± 5 (N = 7) |

Example 6

Bioprobe Targeting MUC-1 Receptor in Breast Cancer

The target on the breast cancer cells may be MUC-1 (Human epithelial mucin, CD277) marker. MUC-1 is highly expressed in many human adenocarcinomas including 80% of breast cancers and is associated with poor prognosis. The ligand on the bioprobe may be an antibody which targets the MUC-1 receptor. Commercial monoclonal mouse anti-human MUC-1 antibodies may be used in preliminary in vitro studies, from such sources as Chemicon International, Temecula, Calif.; and Zymed Laboratories, South San Francisco, Calif. The MUC-1 bioprobes may be formed from 50 nm dextran coated $Fe_3O_4$ particles. The mouse anti-human MUC-1 is a whole antibody and the Fc portion may be linked to the magnetic particle or the dextran coating through several different techniques. A linking agent, such as BS3, available from Pierce, Rockford, Ill., may be used with silanization or the antibody may be biotinylated and attached to a streptavidin-containing, 50 nm dextran coated particle.

In vitro studies demonstrate dose response and proof of killing of cancer cells above the level of the controls. The targeted bioprobes may be further refined by producing Fab and scFV fragments of a monoclonal mouse anti-human MUC-1 antibody, fragments from an antibody library, humanization of the antibody, or production of peptides. Antibodies, fragments, and peptides may be engineered with altered properties such as antigen binding affinity, molecular architecture, and specific receptor epitope targeting to enhance the tumor targeting and potency. The use of fragments, humanized antibody, or peptides creates a ligand that avoids immunogenic response in humans.

The MUC-1 receptor is considered a truly tumor specific antigen because although it is on normal cells, its aberrant glycosylation on tumors creates new epitopes for targeting. The extracellular domain of MUC-1 is shed into the blood stream which makes the selection of the targeting ligand a very important component in this example. The MUC-1 targeting ligand may be selected to avoid the shed portion of the extracellular domain of MUC-1 in the bloodstream. This may result in reducing delivery problems and dilution of the treatment by bioprobes binding to the shed receptor. The MUC-1 targeting ligand recognizes an epitope of MUC-1 which remains on the cancer cell after a portion of the extracellular domain is shed. This choice of ligand allows the bioprobe to specifically and selectively target breast cancer cells.

Example 7

Bioprobe Targeting Non-Small Cell Lung Cancer VEGFR

The bioprobes may be designed to target many different kinds of cancer. A target on non-small cell lung cancer cells may be VEGFR (vascular endothelial growth factor receptor). marker. VEGFR may also be a viable target for many other types of solid cancer tumors. VEGFR has been implicated in tumor induced angiogenesis, or blood vessel growth which has been shown to play an important role in the development of many solid tumors. Angiogenesis is induced by solid tumors to provide nutrients to enable growth. The bioprobe therapy may target tumor-induced angiogenesis and prevent the blood vessel growth needed by a tumor. Since there is little, if any, blood vessel growth in a healthy adult, the targeting of VEGFR should allow for safer treatment options.

Commercial monoclonal mouse anti-human VEGFR antibodies may be used in preliminary in vitro studies, from such sources as Lab Vision Corp., Fremont, Calif. The VEGFR bioprobes may be formed from 50 nm dextran coated $Fe_3O_4$ particles. The mouse anti-human VEGFR is a whole antibody and the Fc portion may be linked to the magnetic particle or the dextran coating through several different techniques. A linking agent, such as $BS^3$, available from Pierce, Rockford, Ill., may be used with silanization or the antibody may be biotinylated and attached to a streptavidin-containing, 50 nm dextran coated particle.

In vitro studies demonstrate dose response and proof of killing of cancer cells above the level of the controls. The targeted bioprobes may be further refined by producing Fab and scFV fragments of a monoclonal mouse anti-human VEGFR antibody, fragments from an antibody library, humanization of the antibody, or production of peptides. Antibodies, fragments, and peptides may be engineered with altered properties such as antigen binding affinity, molecular architecture, and specific receptor epitope targeting to enhance the tumor targeting and potency. The use of fragments, humanized antibody, or peptides creates a ligand that avoids immunogenic response in humans.

Example 8

Bioprobe Targeting Immune System Conditions, CD52

A target rheumatoid arthritis may be cluster designation/differentiation CD52 antigen. CD52 may also be a viable target for other immune system diseases such as multiple sclerosis. For diseases of the patient's immune system, the bioprobe therapy may target the T or B cells of the immune system. Typically these cells are involved in an immune response. T lymphocytes play a central role in initiating and controlling the immune response and the molecular basis for immune recognition and the way the body distinguishes invaders from its own tissues is becoming known. This may bring new insight into a wide range of severe diseases, including rheumatoid arthritis, multiple sclerosis and many others, all of which appear to result in whole or in part from a breakdown of the normal mechanisms of self-tolerance. The damage which occurs in these autoimmune diseases is analogous to the rejection process which occurs after transplantation of a foreign organ. Adults also have active mechanisms for maintaining self-tolerance which are controlled by a complex symphony of interactions between different parts of the immune system. Bioprobes with antibodies to CD52 can destroy lymphocytes and disrupt the immune system at the most fundamental level. Unlike cancer therapy, it may not be the aim to kill all the target cells, but just remove enough to allow a respite for the tissue under attack. The hope was that when the immune system regenerated over the subsequent months, the vicious cycle of tissue injury, resulting in fresh immune stimulation, would have subsided sufficiently for the natural control mechanisms to restore a healthy balance. It may be necessary to monitor T cells during the period of regeneration in order to direct them into a more appropriate pathway of self-tolerance.

Commercial monoclonal rat anti-human CD52 antibodies may be used in preliminary in vitro studies, from such sources as Biosource International, Camerillo, Calif. The CD52 bioprobes may be formed from 50 nm dextran coated $Fe_3O_4$ particles. The mouse anti-human CD52 is a whole antibody and the Fc portion may be linked to the magnetic particle or the dextran coating through several different techniques. A linking agent, such as $BS^3$, available from Pierce, Rockford, Ill., may be used with silanization or the antibody may be biotinylated and attached to a streptavidin-containing, 50 nm dextran coated particle.

The targeted bioprobes may be further refined by producing Fab and scFV fragments of a monoclonal mouse anti-human CD52 antibody, fragments from an antibody library, humanization of the antibody, or production of peptides. Antibodies, fragments, and peptides may be engineered with altered properties such as antigen binding affinity, molecular architecture, and specific receptor epitope targeting to enhance the targeting and potency. The use of fragments, humanized antibody, or peptides creates a ligand that avoids immunogenic response in humans.

Example 9

Bioprobe Targeting Bacterial Conditions

The bioprobes may be designed to target different kinds of pathogen-borne conditions. A pathogen may be any disease producing agent such as, for example, a bacterium, a virus, a microorganism, a fungus, and a parasite. One example of a target for a bacterial pathogen is *Escherichia coli*. *Escherichia coli* is an emerging cause of foodborne illness. Currently, an estimated 73,000 cases of infection and 61 deaths occur in the United States each year. Most illness has been associated with eating undercooked, contaminated ground beef. Person-to-person contact in families and child care centers is also an important mode of transmission. *E. coli* O157:H7 is one of hundreds of strains of the bacterium *Escherichia coli*. Although most strains are harmless and live in the intestines of healthy humans and animals, this strain produces a powerful toxin and can cause severe illness. In this embodiment of the bioprobe therapy, the target is the bacterium itself. The pathogen may be in the blood stream, tissue, or cells. The bioprobe therapy may target and kill the bacteria in the patient. It will also be possible to target infected cells with an appropriate cell surface marker on the cells.

Commercial monoclonal goat anti-*Escherichia coli* O157:H7 antibodies may be used in preliminary in vitro studies, from such sources as Accurate Chemical and Scientific, Westbury, N.Y. The *Escherichia coli* targeted bioprobes may be formed from 50 nm dextran coated $Fe_3O_4$ particles. The goat anti-*Escherichia coli* O157:H7 is a whole antibody and the Fc portion may be linked to the magnetic particle or the dextran coating through several different techniques. A linking agent, such as $BS^3$, available from Pierce, Rockford, Ill., may be used with silanization or the antibody may be biotinylated and attached to a streptavidin-containing, 50 nm dextran coated particle.

In vitro studies demonstrate dose response and proof of killing above the level of the controls. The AMF device will be appropriate to the location of treatment. The targeted bioprobes may be further refined by producing Fab and scFV fragments of a monoclonal goat anti-*Escherichia coli* O157:H7 antibody, fragments from an antibody library, humanization of the antibody, or production of peptides. Antibodies, fragments, and peptides may be engineered with altered properties such as antigen binding affinity, molecular architecture, and specific receptor epitope targeting to enhance the targeting and potency.

Example 10

Bioprobe Targeting Viral Conditions, Hepatitis B

The bioprobes may be designed to target different kinds of pathogen-borne conditions such as a virus. An example of a target for a viral pathogen is Hepatitis B. Hepatitis B is a serious disease caused by a virus that attacks the liver. The virus, which is called hepatitis B virus (HBV), can cause lifelong infection, cirrhosis (scarring) of the liver, liver cancer, liver failure, and death. In this particular embodiment of bioprobe therapy, the target is the virus itself. The pathogen may be in the blood stream, tissue, or cells.

Commercial monoclonal rabbit anti-Hepatitis B antibodies may be used in preliminary in vitro studies, from such sources as Chemicon International, Temecula, Calif. The Hepatitis B bioprobes may be formed from 50 nm dextran coated $Fe_3O_4$ particles. The rabbit anti-Hepatitis B antibody is a whole antibody and the Fc portion may be linked to the magnetic particle or the dextran coating through several different techniques. A linking agent, such as BS³, available from Pierce, Rockford, Ill., may be used with silanization or the antibody may be biotinylated and attached to a streptavidin-containing, 50 nm dextran coated particle.

The AMF device is appropriate to the location of treatment. The targeted bioprobes may be further refined by producing Fab and scFV fragments of a monoclonal mouse anti-Hepatitis B antibody, fragments from an antibody library, humanization of the antibody, or production of peptides. Antibodies, fragments, and peptides may be engineered with altered properties such as antigen binding affinity, molecular architecture, and specific receptor epitope targeting to enhance the targeting and potency.

Example 11

Bioprobe Targeting Viral Conditions, HIV

Another example of a target for a viral pathogen is human immunodeficiency virus, HIV, the cause of AIDS. Although it has long been possible to detect the presence of HIV, scientists have struggled to distinguish infected cells from healthy ones. In this example, the target is associated with the infected cell. For example, when a cell produces HIV, a protein called CTLA4 appears on the cell surface. In this particular example, the CTLA4 protein is used as the bioprobe target. Infected cells tend to hoard copies of the virus inside instead of releasing them steadily after infection. CTLA4 only migrates to the cell's outer surface when the hoarded virus is ready to be released. In this application of bioprobe therapy, the target is the CTLA4 protein marker on infected cells. The cells may be in the blood stream, tissue, or cells. For example, based on a diagnostic test, a patient would use bioprobe therapy when the CTLA4 protein is expressed on the cell surface and the HIV virus is ready to launch. These cells can be destroyed before they have the chance to spread the virus.

Commercial monoclonal rabbit-anti-human CTLA4 antibodies may be obtained from such sources as Chemicon International, Temecula, Calif., and used in preliminary in vitro studies. The CTLA-4 bioprobes may be formed from 50 nm dextran coated $Fe_3O_4$ particles. The monoclonal rabbit-anti-human CTLA4 is a whole antibody and the Fc portion may be linked to the magnetic particle or the dextran coating through several different techniques. A linking agent, such as BS³, available from Pierce, Rockford, Ill., may be used with silanization or the antibody may be biotinylated and attached to a streptavidin-containing, 50 nm dextran coated particle.

The AMF device is be appropriate to the location of treatment. The targeted bioprobes may be further refined by producing Fab and scFV fragments of a monoclonal rabbit-anti-human CTLA4 antibody, fragments from an antibody library, humanization of the antibody, or production of peptides. Antibodies, fragments, and peptides may be engineered with altered properties such as antigen binding affinity, molecular architecture, and specific receptor epitope targeting to enhance the targeting and potency.

Example 12

Bioprobe Targeting Parasitic Conditions

The bioprobes may be designed to target different kinds of parasitic conditions. One example of a target for a parasitic pathogen is *Trypanasoma cruzi*. *Trypanosoma cruzi* is the American form of a parasite that causes Chagas' disease and is transmitted via blood sucking Reduvid bugs. Acute phase symptoms include fever, malaise, lymphatic system abnormalities, and enlargement of the spleen and liver. Fatal pathologies include parasitic infection of the heart or meninges. Chronic manifestations include myocardial damage and arrhythmias, megaesophagus, and megacolon. Diagnosis is by finding the parasite in the blood. In this application of bioprobe therapy, the target is the pathogen itself. The pathogen may be in the blood stream, tissue, or cells. The bioprobe therapy targets and kills the parasite in the patient. It is also possible to target infected cells with an appropriate cell surface marker on the cells.

Commercial monoclonal mouse anti-*Trypanosoma cruzi* antibodies may be used in preliminary in vitro studies, from such sources as Accurate Chemical and Scientific, Westbury, N.Y. The *Trypanosoma cruzi* targeted bioprobes may be formed from 50 nm dextran coated $Fe_3O_4$ particles. The mouse anti-*Trypanosoma cruzi* antibody is a whole antibody and the Fc portion may be linked to the magnetic particle or the dextran coating through several different techniques. A linking agent, such as BS³, available from Pierce, Rockford, Ill., may be used with silanization or the antibody may be biotinylated and attached to a streptavidin-containing, 50 nm dextran coated particle.

The AMF device will be appropriate to the location of treatment. The targeted bioprobes may be further refined by producing Fab and scFV fragments of a monoclonal mouse anti-*Trypanosoma cruzi* antibody, fragments from an antibody library, humanization of the antibody, or production of peptides. Antibodies, fragments, and peptides may be engineered with altered properties such as antigen binding affinity, molecular architecture, and specific receptor epitope targeting to enhance the targeting and potency.

Example 13

Bioprobe Targeting Fungal Conditions

The bioprobes may be designed to target different kinds fungal conditions. One example of a target for a fungal pathogen is be Rhizomucor. Rhizomucor, also known as the *Zygomycetous fungus*, is reported to be allergenic, and may cause mucorosis in immune compromised individuals. Rhizomucor occupies a biological niche similar to Mucor. It is often linked to occupational allergy, and may cause mucorosis in immune-compromised individuals. The sites of infection are the lung, nasal sinus, brain, eye and skin and infection may have multiple sites.

In this application of bioprobe therapy, the target is the pathogen itself. The pathogen may be in the blood stream, tissue, or cells. The bioprobe therapy targets and kills the fungus in the patient. It may also be possible to target infected cells with an appropriate cell surface marker on the cells.

A commercial mouse anti-*Rhizomucor fungus* monoclonal antibody may be used in preliminary in vitro studies, from such sources as DAKO Corp., Carpinteria, Calif. The Rhizomucor targeted bioprobes may be formed from 50 nm dextran coated $Fe_3O_4$ particles. The mouse anti-*Rhizomucor fungus* antibody is a whole antibody and the Fc portion may be linked to the magnetic particle or the dextran coating through several different techniques. A linking agent, such as BS³, available from Pierce, Rockford, Ill., may be used with silanization or the antibody may be biotinylated and attached to a streptavidin-containing, 50 nm dextran coated particle.

The AMF device will be appropriate to the location of treatment. The targeted bioprobes may be further refined by producing Fab and scFV fragments of a monoclonal mouse anti-*Rhizomucor fungus* antibody, fragments from an antibody library, humanization of the antibody, or production of peptides. Antibodies, fragments, and peptides may be engineered with altered properties such as antigen binding affinity, molecular architecture, and specific receptor epitope targeting to enhance the targeting and potency.

Example 14

Bioprobe Targeting Toxins in the Patient

The bioprobes may be designed to target different kinds of toxin in the patient. A toxin is defined as any poison produced by an organism including, but not limited to, bacterial toxins, plant toxins, insect toxin, animal toxins, and man-made toxins. A bacterial toxin target may be, for example, one of Cholera toxin, Diptheria toxin, and Clostridium botulinus toxin. An insect toxin may be, for example, bee venom. An animal toxin may be, for example, the snake toxin, *Crotalus durissus terrificus* venom.

In this example of an application of bioprobe therapy, the target is the toxin itself. The toxin may be in the blood stream, tissue, or cells. The bioprobe therapy may target and destroy the toxin in the patient. In the particular example described here, the target is the bacterial toxin, Cholera.

Commercial monoclonal rabbit anti-Cholera toxin antibodies may be used in preliminary in vitro studies, from such sources as Accurate Chemical and Scientific, Westbury, N.Y. The Cholera-targeted bioprobes may be formed from 50 nm dextran coated $Fe_3O_4$ particles. The rabbit anti-Cholera toxin antibody is a whole antibody and the Fc portion may be linked to the magnetic particle or the dextran coating through several different techniques. A linking agent, such as $BS^3$, available from Pierce, Rockford, Ill., may be used with silanization or the antibody may be biotinylated and attached to a streptavidin-containing, 50 nm dextran coated particle.

The AMF device is appropriate to the location of treatment. The targeted bioprobes may be further refined by producing Fab and scFV fragments of a monoclonal rabbit anti-Cholera toxin antibody, fragments from an antibody library, humanization of the antibody, or production of peptides. Antibodies, fragments, and peptides may be engineered with altered properties such as antigen binding affinity, molecular architecture, and specific receptor epitope targeting to enhance the targeting and potency.

Example 15

Bioprobe Targeting an Undesirable Target

The bioprobes may be designed to target an undesirable target in a patient. An undesirable target is a target that may be associated with a disease or an undesirable condition, but is also present in the normal condition. For example, the target may be elevated or otherwise altered in the disease or undesirable state. The bioprobe may have an affinity for the undesirable target or biological molecules from pathways related to the undesirable target or it may have an affinity for a cell marker or markers associated with the undesirable target.

In this particular example, in arteriosclerosis, a target is low density lipoprotein (LDL). A marker in LDL is apolipoprotein B which can be targeted for bioprobe therapy.

Atherosclerosis is a type of arteriosclerosis involving deposits of fatty substances, cholesterol, cellular waste products, calcium and fibrin (a clotting material in the blood) in the inner lining of an artery.

Atherosclerosis can affect the arteries of the brain, heart, kidneys, other vital organs, and the arms and legs. When atherosclerosis develops in the arteries that supply the brain (carotid arteries), a stroke may occur; when it develops in the arteries that supply the heart (coronary arteries), a heart attack may occur.

In the United States and most other Western countries, atherosclerosis is the leading cause of illness and death. Despite significant medical advances, coronary artery disease (which results from atherosclerosis and causes heart attacks) and atherosclerotic stroke are responsible for more deaths than all other causes combined. Atherosclerosis is a slow, progressive disease that may start in childhood.

In this example of an application of bioprobe therapy, the target is apolipoprotein B. The bioprobe therapy may be used to target, denature, or otherwise deactivate apolipoprotein B found in plaques in the patient. This may prevent or mitigate the deposition of excess LDL or treat the condition.

Commercial monoclonal goat anti-apolipoprotein B antibodies may be used in preliminary in vitro studies, from such sources as Chemicon International, Temecula, Calif. The apolipoprotein B-targeted bioprobes may be formed from 50 nm dextran coated $Fe_3O_4$ particles. The goat anti-apolipoprotein B antibody is a whole antibody and the Fe portion may be linked to the magnetic particle or the dextran coating through several different techniques. A linking agent, such as $BS^3$, available from Pierce, Rockford, Ill., may be used with silanization or the antibody may be biotinylated and attached to a streptavidin-containing, 50 nm dextran coated particle.

The AMF device will be appropriate to the location of treatment. The targeted bioprobes may be further refined by producing Fab and scFV fragments of a monoclonal goat anti-apolipoprotein B antibody, fragments from an antibody library, humanization of the antibody, or production of peptides. Antibodies, fragments, and peptides may be engineered with altered properties such as antigen binding affinity, molecular architecture, and specific receptor epitope targeting to enhance the targeting and potency.

Example 16

Bioprobe Associated with Reaction to an Organ Transplanted into the Patient

The bioprobes may be designed to target cells, tissue, or biological molecules involved in a reaction to an organ transplanted into the patient. This application is similar to diseases of the patient's immune system. The bioprobe therapy may target the T or B cells of the immune system. Typically these cells are involved in an immune response. T lymphocytes play a central role in initiating and controlling the immune response and the molecular basis for immune recognition and the way the body distinguishes invaders from its own tissues is becoming known. The damage which occurs in the rejection process which occurs after transplantation of a foreign organ is analogous to autoimmune diseases. Bioprobes which can destroy lymphocytes and disrupt the immune system at the most fundamental level can be used to treat organ transplant rejection. Unlike cancer therapy, it may not be the aim to kill all the target cells, but just remove enough to allow a respite for the tissue under attack. The hope was that when the immune system regenerated over the subsequent months, the vicious cycle of tissue injury, resulting in fresh immune stimulation would have subsided sufficiently for the natural control mechanisms to restore a healthy balance. It may be necessary to monitor T cells during the period of regeneration in order to direct them into a more appropriate pathway of self-tolerance.

In this particular example, the bioprobe target is the CD52 antigen on T cells. CD52 antigen has been associated with kidney and bone marrow transplantation. Commercial monoclonal rat anti-human CD52 antibodies may be used in preliminary in vitro studies, from such sources as Biosource International, Camerillo, Calif. The CD52 bioprobes may be formed from 50 nm dextran coated $Fe_3O_4$ particles. The mouse anti-human CD52 is a whole antibody and the Fc portion may be linked to the magnetic particle or the dextran coating through several different techniques. A linking agent, such as $BS^3$, available from Pierce, Rockford, Ill., may be used with silanization or the antibody may be biotinylated and attached to a streptavidin-containing, 50 nm dextran coated particle.

The AMF device will be appropriate to the location of treatment. The targeted bioprobes may be further refined by producing Fab and scFV fragments of a monoclonal mouse anti-human CD52 antibody, fragments from an antibody library, humanization of the antibody, or production of peptides. Antibodies, fragments, and peptides may be engineered with altered properties such as antigen binding affinity, molecular architecture, and specific receptor epitope targeting to enhance the targeting and potency.

Example 17

Bioprobe Targeting Non-Cancerous Disease Material

The bioprobes may be designed to target cells, tissue, or biological molecules related to a non-cancerous disease. One particular example of a target related to a non-cancerous disease is B protein and its deposits associated with Alzheimer's disease. Bioprobes designed to specifically bond to lipoproteins that transport amyloids in the vascular system can be used to target, denature, or otherwise deactivate these lipoproteins when exposed to AMF treatment. This may prevent or mitigate the deposition of excess amyloids in various organs of humans or animals (amyloidosis) or treat the condition. Similarly bioprobes can be used to target, denature or otherwise deactivate amyloids directly to prevent or treat the deposition of excess amyloids.

A common form of amyloidosis is Alzheimer's disease. Although not fully understood, the accumulation of amyloid protein in the brain to form plaque (amyloid fibrils) is part of the pathology. Bioprobes which are designed to specifically bond to the lipoprotein, amyloid B protein, associated with Alzheimer's disease, as they are transported in the vascular system or after they are deposited in the brain, can be used to target, denature or otherwise deactivate these lipoproteins. The residual amyloid proteins may be absorbed or otherwise removed from the body.

The bioprobe target is amyloid B protein. Commercial monoclonal rabbit anti-amyloid B protein antibodies may be used in preliminary in vitro studies, from such sources as Accurate Chemical and Scientific, Westbury, N.Y. The amyloid B protein targeted bioprobes may be formed from 50 nm dextran coated $Fe_3O_4$ particles. The rabbit anti-amyloid B protein antibody is a whole antibody and the Fc portion may be linked to the magnetic particle or the dextran coating through several different techniques. A linking agent, such as $BS^3$, available from Pierce, Rockford, Ill., may be used with silanization or the antibody may be biotinylated and attached to a streptavidin-containing, 50 nm dextran coated particle.

The AMF device will be appropriate to the location of treatment. The targeted bioprobes may be further refined by producing Fab and scFV fragments of a monoclonal rabbit anti-amyloid B protein antibody, fragments from an antibody library, humanization of the antibody, or production of peptides. Antibodies, fragments, and peptides may be engineered with altered properties such as antigen binding affinity, molecular architecture, and specific receptor epitope targeting to enhance the targeting and potency.

Example 18

Bioprobe Targeting a Proteinaceous Pathogen

The bioprobes may be designed to target cells, tissue, or biological molecules related to a proteinaceous pathogen. An example of a target is prion protein 3F4 associated with prion diseases known as transmissible spongiform encephalopathies. Novel infectious particles, termed prions, composed largely and perhaps solely of a single protein, are the likely causative agents of a group of transmissible spongiform encephalopathies that produce lethal decline of cognitive and motor function. Evidence indicates that the responsible protein arrives at a pathogenic state by misfolding from a normal form that has ubiquitous tissue distribution.

Bioprobes designed to specifically bond to prions such as Prion protein 3F4 can be used to target, denature, or otherwise deactivate these prions when exposed to AMF treatment. This may prevent, mitigate, or treat the condition. Commercial monoclonal mouse anti-human prion protein 3F4 antibodies may be used in preliminary in vitro studies, from such sources as DAKO Corp., Carpinteria, Calif. The prion protein 3F4-targeted bioprobes may be formed from 50 nm dextran coated $Fe_3O_4$ particles. The mouse anti-human prion protein 3F4 antibody is a whole antibody and the Fc portion may be linked to the magnetic particle or the dextran coating through several different techniques. A linking agent, such as $BS^3$, available from Pierce, Rockford, Ill., may be used with silanization or the antibody may be biotinylated and attached to a streptavidin-containing, 50 nm dextran coated particle.

The AMF device is appropriate to the location of treatment. The targeted bioprobes may be further refined by producing Fab and scFV fragments of a mouse anti-human prion protein 3F4 antibody, fragments from an antibody library, humanization of the antibody, or production of peptides. Antibodies, fragments, and peptides may be engineered with altered properties such as antigen binding affinity, molecular architecture, and specific receptor epitope targeting to enhance the targeting and potency.

Example 19

Bioprobe Targeting a Hormone-Related Disease

The bioprobes may be designed to target cells, tissue, or biological molecules related to a hormone disease. In one particular example, growth hormone is a peptide anterior pituitary hormone essential for growth. The hypothalamus maintains homeostatic levels of growth hormone. Cells under the action of growth hormone increase in size (hypertrophy) and number (hyperplasia). Growth hormone also causes increase in bone length and thickness by deposition of cartilage at the ends of bones. During adolescence, sex hormones cause replacement of cartilage by bone, halting further bone growth even though growth hormone is still present. Too much growth hormone can cause gigantism. Bioprobes designed to target human growth hormone can be used to denature, or otherwise deactivate excess hormone when exposed to AMF treatment Commercial monoclonal rabbit anti-human growth hormone antibodies may be used in preliminary in vitro studies, from such sources as Accurate Chemical and Scientific, Westbury, N.Y.

In another example, overproduction of the female hormone estrogen may increase the risk for breast cancer. The number of new cancer cells increases proportionally to the amount of overexpression by the estrogen precursor—and these effects may be prevented, mitigated, or treated using bioprobe therapy. Bioprobes designed to target estrogen can be used to denature, or otherwise deactivate excess hormone when exposed to AMF treatment. Commercial monoclonal rabbit anti-estrogen antibodies may be used in preliminary in vitro studies, from such sources as US Biological, Swampscott, Mass.

Example 20

Extracorporeal Approach to Bioprobe Therapy

In extracorporeal hyperthermal therapy, bioprobes may be used to lyse, denature, or otherwise deactivate the disease material by circulating the blood outside of the body, exposing it to AMF, and returning it to the body. The bioprobes may be introduced into the vascular circulating system or into the blood circulating outside of the body. For example, to target bioprobe/target complexes that are carried primarily in the blood serum or plasma, the blood serum or plasma may be extracorporeally separated from the other blood components, exposed to AMF to destroy the target, and recombined with the other blood components before returning the blood to the body. The bioprobes may be introduced into the vascular circulating system, the blood circulating outside of the body, or the blood serum or plasma after it is separated. In another embodiment, the bioprobes may be contained in a vessel or column through which the blood circulating outside of the body or the blood serum or plasma flows. The vessel or column may be exposed to AMF to destroy the targeted cells or antigens before returning the blood to the body.

The advantages of exposing bioprobes to AMF, and heating outside of the body include the ability to heat to higher temperatures and/or heat more rapidly to enhance efficacy wile minimizing heating and damage to surrounding body tissue, and reducing exposure of the body to AMF energy. If the bioprobes are introduced into the blood circulating outside the body or the blood serum or plasma after being extracted from the body, advantages include i) no introduction of ferromagnetic bioprobes directly into the body and ii) higher concentrations of bioprobes to targeted cells or antigens. In addition, the bulk blood or blood serum/plasma can be cooled externally by a variety of means as it is being heated by the bioprobes, which will not mitigate the localized heating by the bioprobe, or after the heating, but before returning it to the body.

The treated bioprobes and associated targets need not be returned to the patient's body. For example, if the bioprobes and associated targets are contained in blood extracted from a patient, the treated bioprobes and associated targets may be separated from the blood before the blood is returned to the patient's body. One approach for separating the bioprobes and associated targets from the extracted bodily materials is to pass the bodily fluids containing the bioprobes and associated targets through a magnetic field gradient. This provides an advantage in reducing the amount of treated disease material returned to the patient's body.

Example 21

Pretargeting Approach to Bioprobe Therapy

A pretargeting therapy approach to the bioprobes may be used to achieve higher concentration of bioprobes at the targeted site. Pretargeting therapy may also allow for higher doses of ligand or multiple doses of the ligand to be given to the patient and may allow for more time for the ligand to localize at the predetermined target. In pretargeting therapy, the targeting ligand is infused into the body separately from the magnetic material composition and allowed to accumulate at the target site. For example, the ligand may be comprised of an antigen-binding portion to bind the antigen at the target site and a high affinity binding site for a small molecule. A clearing agent may be infused to remove unbound ligand circulating in the bloodstream. The magnetic material composition linked to the small molecule is the added. The magnetic material travels to the targeted site and attaches to the ligand bound at the treatment site. For example, a streptavidin conjugated antibody may be used with a biotinylated magnetic particle composition. The antibody is typically administered to the patient prior to the magnetic particle and allowed to localize at the predetermined target. Since the pretargeting antibody is typically non-toxic, high doses may be given. A clearing agent may or may not be used to remove unbound antibody depending on the residence time in the body. The biotinylated magnetic particle composition is administered to the patient at an appropriate time for bioprobe therapy. The streptavidin conjugated antibody and biotinylated magnetic particle may combine in the patient's body prior to bioprobe therapy. The strong biotin-streptavidin association is used to bind the magnetic particle to the antibody in the patient.

Example 22

Temperature Monitoring During Treatment

In a treatment cycle, the bioprobes 210 may be exposed to and become attached to metastatic cells in the treatment area. Pole pieces 204 may be chosen to provide treatment in a selected treatment area, for example, approximately 6 inches in diameter. The patient 105 is typically placed on the treatment bed 206, and the bed controller 108 is typically adjusted to place the targeted tissue at the region of maximum field strength between the poles 204. The pulse width, duty cycle, and peak amplitude of the AMF and the treatment time may be adjusted. Several temperature probes, for example, four temperature probes, may be inserted into the treatment volume. One probe may be located centrally and the other three may be inserted into tissues, within the treatment area that are heated by the AMF. As the tissue heats under the applied AMF, the temperature probes 354 send data to the probe monitor 352. The monitor sends the temperature data via the feedback loop 324 to the RF generator controller 356. Monitoring may be continuous, for example at a data rate of 10 samples per second and the duty of the RF generator 318 may be adjusted once per second based on individual, 10 sample averages from each probe. If none of the probes 354 sense a temperature greater than the preset limit, the RF generator 318 may be permitted to operate at the original settings. If one or more of the probes 354 senses a temperature over the preset threshold, the controller 356 may send a command to reduce at least one of the duty cycle, the PRF, the magnitude of the magnetic field. This process continues until the treatment is completed.

Example 23

Preliminary Temperature Monitoring to Optimize Treatment

Using the temperature probes described in Example 22 or an infrared thermal monitor, a practical map of the field strength can be attained by operating at a reduced power level and monitoring the tissue temperature in and around the desired treatment area. This information may be used to adjust the operating parameters of the auxiliary coils. Any or all of the following auxiliary coil operating parameters may be adjusted manually and/or automatically, based upon the tissue temperature map; i. Auxiliary coil peak current, ii. Auxiliary coil pulse width, iii Auxiliary coil current phase, relative to primary coil current. When the temperature difference between the tissue in the treatment area and the surrounding tissue is maximized, then the auxiliary coils' operating parameters have been optimized for the given auxiliary coils' positions. This preliminary adjustment may be performed using a suitable tissue model thereby reducing the patient's exposure and discomfort.

While the above description of the invention has been presented in terms of a human patient, it is appreciated that the invention may also be applicable to treating disease in other mammals.

As noted above, the present invention is applicable to a magnetic material composition, a system and method of thermotherapy for the treatment of at least cancerous tissue, non-cancerous disease material. The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those skilled in the art to which the present invention is directed upon review of the present specification. The claims are intended to cover such modifications and devices.

We claim:

1. A method for treating a patient, comprising:
   administering a magnetic material composition to at least a position of the patient, the magnetic material composition comprising at least one, single domain magnetic particle attached to a ligand specific to a predetermined target in the patient, said single domain magnetic particle capable of producing heat by Neél relaxation in response to ap alternating magnetic field; and applying an alternating magnetic field to the magnetic material composition combined with the predetermined target to inductively heat the magnetic material composition.

2. The method as recited in claim 1, wherein the predetermined target is associated with a cancer.

3. The method as recited in claim 2, wherein the predetermined target is one of a) a member of vascular endothelial growth factor receptor (VEGFR) family, b) a member of carcinoembryonic antigen (CEA) family, c) an anti-idiotypic mAR, d) a ganglioside mimic, e) a member of cluster designation/differentiation (CD) antigen family, f) a member of epidermal growth factor receptor (EGFR) family. g) a cellular adhesion molecule, h) a member of MUC-type inucin family, i) a cancer antigen (CA), j) a matrix metalloproteinase, k) a glycoprotein antigen, l) a melanoma associated antigen (MAA), m) a proteolytic enzyme, n) a calmodulin, o) a tumor necrosis factor (TNF) receptor family, p) an angiogenic marker, q) a melanoma antigen recognized by T cells (MART) antigen, r) a member of melanoma antigen encoding gene (MAGE) family, s) a prostate membrane specific antigen (PMSA), t) a small cell lung carcinoma antigen (SCLCA), u) a proliferating cell nuclear antigen 10 (PC10), v) pS2, w) a T/Tn antigen, x) a hormone receptor, y) a tumor suppressor gene antigen, z) a cell cycle regulator antigen, aa) an oncogene antigen, bb) an oncogene receptor antigen, cc) a proliferation marker, dd) a proteinase involved in degradation of extracellular matrix, ee) a malignant transformation related factor, ff) an apoptosis-related factor gg) a human carcinoma antigen and hh) any combination of a) through gg).

4. The method as recited in claim 3, wherein the ganglioside mimic is GD3.

5. The method as recited in claim 3, wherein the epidermal growth factor receptor (EGFR) includes at least one of Her-1, Her-2, Her-3, Her-4, and any combination thereof.

6. The method as recited in claim 3, wherein the cluster designation/differentiation antigen includes at least one of CD20 antigen, CD22 antigen, CD52 antigen, CD64 antigen, CD31 antigen, CD33 antigen and any combination thereof.

7. The method as recited in claim 3, wherein the cellular adhesion molecule is epithelial cellular adhesion molecule (Ep-CAM) antigen.

8. The method as recited in claim 3, wherein to MUC-type mucin includes at least one of polymorphic epithelial mucin (PEM), and MUC-1, and any combination thereof.

9. The method as recited in claim 3, wherein the cancer antigen is at least one of CA125, CA19-9, CA15-3 (breast tumor antigen), and CA242, and any combination thereof.

10. The method as recited in claim 3, wherein the matrix metalloproteinase is matrix metalloproteinase 2 (MMP-2).

11. The method as recited in claim 3, wherein the glycoprotein antigen is epithelial associated glycoprotein (HM-FGI antigen).

12. The method as recited in claim 3, wherein the proteolytic enzyme is at least one of cathepsin G, cathepsin D, cathepsin L, cathepsin B, cathepsin C, and cathepsin S, and any combination thereof.

13. The method as recited in claim 3, wherein the calmodulin is calponin.

14. The method as recited in claim 3, wherein the tumor necrosis factor receptor is a TRAIL Receptor-1 protein.

15. The method as recited in claim 3, wherein the angiogenic marker is at least one of vascular endothelial growth factor receptor (VEGFR), Integrin alpha.v.beta.3, and any combination thereof.

16. The method as recited in claim 1, wherein the predetermined target is associated with a disease of a patient's immune system.

17. The method as recited in claim 16, wherein the predetermined target is an antigen associated with one of rheumatoid arthritis, vasculitis and multiple sclerosis.

18. The method as recited in claim 17, wherein the predetermined target is a cluster designation/differentiation antigen.

19. The method as recited in claim 1, wherein the predetermined target is a virus.

20. The method as recited in claim 19, wherein the predetermined target is Epstein-Barr virus (EBV).

21. The method as recited in claim 19, wherein the predetermined target is a Hepatitis virus.

22. The method as recited in claim 19, wherein the predetermined target is a human immunodeficiency virus (HIV).

23. The method as recited in claim 19, wherein the predetermined target is a Herpes virus.

24. The method as recited in claim 1, wherein the predetermined target is one of an undesirable material and associated with an undesirable material.

25. The method as recited in claim 24, wherein the predetermined target is undesired adipose tissue.

26. The method as recited in claim 24, wherein the predetermined target is a gastric inhibitory polypeptide receptor.

27. The method as recited in claim 24, wherein the predetermined target is low density lipoprotein (LDL).

28. The method as recited in claim 24, wherein the predetermined target is clotted blood.

29. The method as recited in claim 1, wherein the predetermined target is associated with a reaction to an organ transplanted into the patient.

30. The method as recited in claim 29, wherein the predetermined target is at least one of human T cell receptor CD3 antigen, CD4 antigen, CD8 antigen, CD18 antigen, CD52 antigen and CD154 antigen.

31. The method as recited in claim 1, wherein the predetermined target is one of non-cancerous disease material and associated with non-cancerous disease material.

32. The method as recited in claim 31, wherein the predetermined target is one of a non-cancerous disease deposit and a non-cancerous disease precursor deposit.

33. The method as recited in claim 32, wherein the predetermined target is associated with Alzheimer's disease.

34. The method as recited in claim 33, wherein the predetermined target is an amyloid protein.

35. The method as recited in claim 33, wherein the predetermined target is an apolipoprotein.

36. The method as recited in claim 31, wherein the predetermined target is associated with an HIV infected cell.

37. The method as recited in claim 36, wherein the predetermined target is CTLA4 protein.

38. The method as recited in claim 1, wherein administering the magnetic material composition further comprises administering the material to a specific area of a patient's body via an administration technique being at least one of injecting the composition intravenously, injecting the composition intraperitoneally, injecting the composition intravascularly, injecting the composition intramuscularly, injecting the composition subcutaneously, applying the composition topically, applying the composition via a wash, lavage or rinse perisurgically, inhaling the composition, orally ingesting the composition, and rectally inserting the composition.

39. The method as recited in claim 1, wherein administering the magnetic material composition further comprises: administering the ligand and the magnetic particle to the patient separately; and combining the ligand with the magnetic particle in the patient's body.

40. The method as recited in claim 39, wherein administering the magnetic material composition further comprises: administering the ligand, having one of a binder and a receptor, to the patient; administering the magnetic particle, having the other of the binder and the receptor to the patient; and combining the ligand with the magnetic particle by uniting the binder and receptor in the patient's body.

41. The method as recited in claim 40, wherein the binder is biotinylated and the receptor is an avidin.

42. The method as recited in claim 39, wherein administering the magnetic material composition further comprises: administering a bispecific ligand to the patient; administering a magnetic material conjugated to a target molecule to the patient; and combining the magnetic particle with the ligand in the patient's body.

43. The method as recited in claim 1, wherein applying the alternating magnetic field includes applying the alternating magnetic field when the magnetic material composition is outside the patient's body.

44. The method as recited in claim 43, wherein administering comprises providing the magnetic material composition within the patient's body and extracting the magnetic material composition from the patient's body after attaching to the target.

45. The method recited in claim 43, further comprising removing, after applying the alternating magnetic field, the magnetic material composition from extracted bodily materials and prior to returning the extracted bodily materials to the patient's body.

46. The method as recited in claim 43, wherein administering comprises extracorporeal administration of the magnetic material composition into a patient's bodily materials.

47. The method as recited in claim 46, wherein extracorporeal administration comprises: extracting bodily materials from the patient; administering the magnetic material composition to the extracted bodily materials; and exposing the extracted bodily materials to the alternating magnetic field.

48. The method as recited in claim 43, further comprising returning extracted bodily materials to the patient's body after exposure to the alternating magnetic field.

49. The method as recited in claim 43, further comprising returning extracted bodily materials to the patient's body before exposure to the magnetic field.

50. The method as recited in claim 43, wherein the magnetic material composition is in at least one of blood and blood products extracted from the patient.

51. The method as recited in claim 1, further comprising detecting at least one location of accumulation of the magnetic material composition within the patient's body.

52. The method as recited in claim 51, wherein detecting the at least one location of accumulation of the magnetic material includes using at least one of i) magnetic resonance imaging (MRI) and ii) a superconducting quantum interference device (SQUID) after administering the composition to the patient and prior to application of the alternating magnetic field.

53. The method as recited in claim 52, further comprising determining an amount of the magnetic material composition taken up by the target by direct or indirect detection of the particles via at least one of MRI and the SQUID.

54. The method as recited in claim 53, wherein the determined amount of magnetic material composition taken up by the target is used to calculate a condition and duration of the alternating magnetic field to be applied.

55. The method as recited in claim 1, further comprising inducing a desired pathological effect by inductively heating the magnetic material causing one of necrosis, apoptosis and deactivation of disease material.

56. The method as recited in claim 1, further comprising applying the alternating magnetic field to a region of the patient containing the predetermined target and to a region of the patient adjacent to the region containing the predetermined target.

57. The method as recited in claim 1, further comprising localizing the magnetic material composition to a region containing the predetermined target by applying a d.c. component of the alternating magnetic field to the region of the patient containing the predetermined target.

58. The method as recited in claim 1, further comprising monitoring at least one physical characteristic of a portion of the patient.

59. The method as recited in claim 58, wherein monitoring the at least one physical characteristic comprises monitoring temperature.

60. The method as recited in claim 58, wherein monitoring the at least one physical characteristic comprises monitoring tissue impedance.

61. The method as recited in claim 1, wherein the alternating magnetic field is applied to the patient during a treatment duration, and applying the alternating magnetic field comprises pulsing the alternating magnetic field with a pulse length less than the treatment duration.

62. The method as recited in claim 61, further comprising applying at least two pulses of the alternating magnetic field to the patient.

63. The method as recited in claim 1, further comprising generating with a magnetic field generator an alternating magnetic field having a strength in the range of about 100 Oersteds (Oe) to about 2,000 Oe proximate the magnetic field generator.

64. The method as recited in claim 1, wherein the alternating magnetic field has one of a triangular waveform, square waveform, sinusoidal waveform, trapezoidal waveform and a sawtooth waveform.

65. The method as recited in claim 1, wherein applying the alternating magnetic field comprises modulating the alternating magnetic field.

66. The method as recited in claim 65, wherein modulating the magnetic field comprises applying a modulation having one of a sinusoidal envelope, a triangular envelope, a square wave envelope, a trapezoidal envelope, and a sawtooth envelope.

67. The method as recited in claim 1, wherein applying the alternating magnetic field comprises providing and positioning auxiliary coils to influence a magnetic field pattern generated by a primary coil.

68. The method as recited in claim 67, further comprising driving at least one of the primary and auxiliary coils with a d.c. component to influence the magnetic field pattern.

69. The method as recited in claim 68, wherein the d.c. component has a magnitude sufficient to influence the magnetic field pattern by causing the alternating magnetic field to have at least one of i) a unidirectional nature with varying intensity and ii) a time-averaged, non-zero value.

70. The method as recited in claim 67, further comprising driving the auxiliary coils in series with the primary coil.

71. The method as recited in claim 67, further comprising driving the auxiliary coils in parallel with the primary coil.

72. The method as recited in claim 67, further comprising electrically matching the auxiliary coils with a phase relationship so as to maximize the field strength in a specific area and minimizing the field strength in areas which may experience detrimental effects from the alternating magnetic field.

73. The method as recited in claim 67, further comprising influencing the magnetic field pattern to separate the patient from an electric field component associated with the magnetic field, so as to reduce dielectric heating of the patient.

74. The method as recited in claim 67, wherein applying the alternating magnetic field comprises applying the alternating magnetic field using only the primary coil.

75. The method as recited in claim 1, wherein applying the alternating magnetic field further comprises providing a primary coil as a core-less coil.

76. The method as recited in claim 1, wherein applying the alternating magnetic field includes generating the alternating magnetic field with a magnetic field generator and further comprises cooling the magnetic field generator with liquid.

77. The method as recited in claim 76, further comprising cooling a core of the magnetic field generator with liquid.

78. The method as recited in claim 1, wherein applying the alternating magnetic field includes driving a primary coil formed of at least first and second coils, the first and second coils disposed proximate respective first and second pole pieces of a magnetic core.

79. The method as recited in claim 1, wherein applying the alternating magnetic field further includes driving a plurality of coils located along a magnetic core.

* * * * *